United States Patent
George et al.

(10) Patent No.: US 11,666,630 B2
(45) Date of Patent: Jun. 6, 2023

(54) POLYPEPTIDES FOR MANAGING VIRAL INFECTIONS

(71) Applicants: EMORY UNIVERSITY, Atlanta, GA (US); RAJIV GANDHI CENTRE FOR BIOTECHNOLOGY, Thiruvananthapuram (IN)

(72) Inventors: Sanil George, Thimvananthapuram (IN); Joshy Jacob, Snellville, GA (US); David Holthausen, Atlanta, GA (US); Song Hee Lee, Atlanta, GA (US); Jessica Shartouny, Atlanta, GA (US)

(73) Assignees: Emory University, Atlanta, GA (US); Rajiv Gandhi Centre for Biotechnology, Thiruvananthapuram (IN)

( * ) Notice: Subject to any disclaimer, the term of this patent is extended or adjusted under 35 U.S.C. 154(b) by 0 days.

(21) Appl. No.: 17/127,161

(22) Filed: Dec. 18, 2020

(65) Prior Publication Data

US 2021/0138029 A1    May 13, 2021

Related U.S. Application Data

(62) Division of application No. 16/469,119, filed as application No. PCT/US2017/064330 on Dec. 1, 2017, now Pat. No. 10,898,544.

(60) Provisional application No. 62/466,066, filed on Mar. 2, 2017, provisional application No. 62/433,490, filed on Dec. 13, 2016.

(51) Int. Cl.
| | |
|---|---|
| *A61K 38/17* | (2006.01) |
| *A61K 38/46* | (2006.01) |
| *A61K 38/00* | (2006.01) |
| *A61K 45/06* | (2006.01) |
| *A61P 31/16* | (2006.01) |
| *C07K 14/46* | (2006.01) |
| *C12N 15/00* | (2006.01) |

(52) U.S. Cl.
CPC .............. *A61K 38/17* (2013.01); *A61K 38/46* (2013.01); *A61K 45/06* (2013.01); *A61P 31/16* (2018.01); *C07K 14/463* (2013.01); *C12N 15/00* (2013.01); *A61K 38/00* (2013.01)

(58) Field of Classification Search
CPC ........ A61K 38/00; A61K 38/17; A61K 38/46; A61K 45/06; A61P 31/16; C07K 14/463; C07K 14/46
See application file for complete search history.

(56) References Cited

U.S. PATENT DOCUMENTS

| | | | | | |
|---|---|---|---|---|---|
| 4,966,848 | A | * | 10/1990 | Smith | C12N 9/1029 435/942 |
| 5,223,421 | A | * | 6/1993 | Smith | C12N 9/1029 435/255.2 |
| 5,837,218 | A | * | 11/1998 | Peers | C07K 14/001 424/1.65 |
| 7,862,826 | B2 | | 1/2011 | Murphy et al. | |
| 9,464,124 | B2 | | 10/2016 | Bancel et al. | |
| 10,898,544 | B2 | | 1/2021 | George | |
| 2007/0207209 | A1 | | 9/2007 | Murphy et al. | |
| 2012/0070417 | A1 | | 3/2012 | Batycky et al. | |
| 2014/0296137 | A1 | | 10/2014 | Rajamani et al. | |
| 2015/0056253 | A1 | | 2/2015 | Bancel et al. | |

FOREIGN PATENT DOCUMENTS

| | | |
|---|---|---|
| WO | WO 1998/25961 | 3/2013 |
| WO | WO 2013/039857 A1 | 3/2013 |

OTHER PUBLICATIONS

Database UniProt EBI Accession No. EIB2U1, 1 page, (Nov. 2, 2010).
Database UniProt EBI Accession No. E1B2U3, 1 page, (Nov. 2, 2010).
Holthausen et al., "An amphibian host defense peptide is virucidal for human H1 hemagglutinin-bearing influenza viruses," *Immunity* 46(4):587-595 (Apr. 18, 2017).
International Search Report and Written Opinion from the parent PCT Application No. PCT/US2017/064330, 8 pages dated Mar. 12, 2019).
Kumar et al., "First report of lividin and spinulosain peptides from the skin secretion of an Indian frog," *Acia Biologica Hungarica* 67(1): 121-124 (2016).
Reshmy et al., "Three novel antimicrobial peptides from the skin of the Indian bronzed frog *Hylarana temporalis* (Anura: Ranidae)," *Journal of Peptide Science* 17(5) 342-347 (Epub Mar. 15, 2011).
Yang et al., "Induction of antimicrobial peptides from Rana dybowskii under Rana grylio virus stress, and bioactivity analysis," *Canadian Journal of Microbiol* 58(7):848-855 (Epub 2012 Jun. 15, 2012)(Abstract).
Lee et al. The amphibian peptide Yodha is virucidal for Z 1. SMLLLFFLGTISLSLCQDDQERC SEQ ID NO: 1
2. AMLLLFFLGTISLSLCQDDQERC SEQ ID NO: 2
3. SALLLFFLGTISLSLCQDDQERC SEQ ID NO: 3
4. SMALLFFLGTISLSLCQDDQERC SEQ ID NO: 4
5. SMLALFFLGTISLSLCQDDQERC SEQ ID NO: 5
6. SMLLAFFLGTISLSLCQDDQERC SEQ ID NO: 6
7. SMLLLAFLGTISLSLCQDDQERC SEQ ID NO: 7
8. SMLLLFALGTISLSLCQDDQERC SEQ ID NO: 8
9. SMLLLFFAGTISLSLCQDDQERC SEQ ID NO: 9
10. SMLLLFFLATISLSLCQDDQERC SEQ ID NO: 10
11. SMLLLFFLGAISLSLCQDDQERC SEQ ID NO: 11
12. SMLLLFFLGTASLSLCQDDQERC SEQ ID NO: 12
13. SMLLLFFLGTIALSLCQDDQERC SEQ ID NO: 13
14. SMLLLFFLGTISASLCQDDQERC SEQ ID NO: 14
15. SMLLLFFLGTISLALCQDDQERC SEQ ID NO: 15
16. SMLLLFFLGTISLSACQDDQERC SEQ ID NO: 16
17. SMLLLFFLGTISLSLAQDDQERC SEQ ID NO: 17
18. SMLLLFFLGTISLSLCADDQERC SEQ ID NO: 18
19. SMLLLFFLGTISLSLCQADQERC SEQ ID NO: 19
20. SMLLLFFLGTISLSLCQDAQERC SEQ ID NO: 20
21. SMLLLFFLGTISLSLCQDDAERC SEQ ID NO: 21
22. SMLLLFFLGTISLSLCQDDQARC SEQ ID NO: 22
23. SMLLLFFLGTISLSLCQDDQEAC SEQ ID NO: 23
24. SMLLLFFLGTISLSLCQDDQERA SEQ ID NO: 24

FIG. 6A

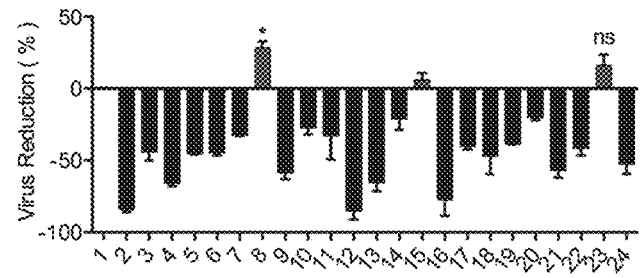

FIG. 6B

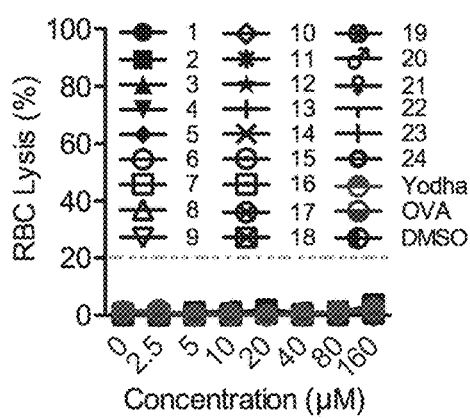

FIG. 6C

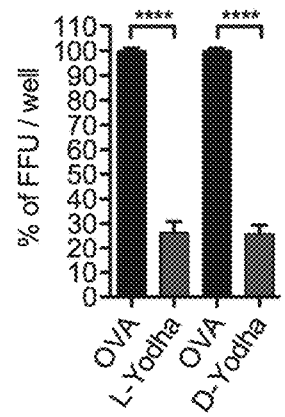

FIG. 6D

| | Peptide Sequences | | Source | Genebank Accession# |
|---|---|---|---|---|
| Yodha | SMLLLFFLGTISLSLCQDDQERC | SEQ ID NO: 1 | Hylarana aurantiaca | This study |
| Variant.1 | SMLLLFFLGTISLSLCQDERGA | SEQ ID NO: 25 | Rana ornativentris | BAI53089 |
| Variant.2 | SMLLLFFLGTISLSLCQDEGA | SEQ ID NO: 26 | Rana dybowskii | AEK25126 |
| Variant.3 | SMLLLFFLGTISLSLCQEEERGA | SEQ ID NO: 27 | Rana kukunoris | AFP24867 |
| Variant.4 | SMLLLFFLGTISLSLCEQERNA | SEQ ID NO: 28 | Odorrana grahami | ABK58825 |
| Variant.5 | SMLLLFFLGTISLSLCEQERDSD | SEQ ID NO: 29 | Sylvirana latouchii | CDN67484 |
| Variant.6 | SMLLLFFLGTISLSLCEQERDAD | SEQ ID NO: 30 | Odorrana schmackeri | CDI30156 |
| Variant.7 | SMLLLFFLGTISLSLCQEERGA | SEQ ID NO: 31 | Rana tagoi okiensis | BAJ07382 |
| Variant.8 | SMLLLFFLGTISLSLCEEERNA | SEQ ID NO: 32 | Amolops loloensis | AFX61483 |
| Variant.9 | SMLLLFFLGTISLSLCQEERDA | SEQ ID NO: 33 | Rana amurensis | CAJ80863 |
| Variant.10 | SLLLLFFLGTISLSLCQDETNA | SEQ ID NO: 34 | Odorrana andersonii | ACZ71263 |
| Variant.11 | SLLLLFFLGTINLSLCQDDEMPK | SEQ ID NO: 35 | Odorrana andersonii | ADP06153 |
| Variant.12 | PMLLLFFLGTISLSLCQEERGA | SEQ ID NO: 36 | Rana kukunoris | AIU99803 |
| Variant.13 | SMLLLFFLGTINLSLCQEERDA | SEQ ID NO: 37 | Odorrana ishikawae | BAK93309 |
| Variant.14 | SLLLLFFLGTISLSLCQEEERNA | SEQ ID NO: 38 | Odorrana andersonii | ADP06113 |
| Variant.15 | SMLLLFFLGMISLSLCQDERGA | SEQ ID NO: 39 | Sylvirana latouchii | ACM67502 |
| Variant.16 | MLLLFFLGTISLSLCEQERNA | SEQ ID NO: 40 | Odorrana andersonii | ABK58825 |
| Variant.17 | SMLLLFFLGTINLSLCEQERDA | SEQ ID NO: 41 | Amolops hainanensis | AEZ52967 |
| Variant.18 | PMLLLFFLGTISLSLCEQERNA | SEQ ID NO: 42 | Odorrana andersonii | ACZ71283 |
| Variant.19 | SMLLLFFLGTINLSLCEQERNA | SEQ ID NO: 43 | Amolops hainanensis | AEZ52956 |
| Variant.20 | SLLLLFFLGTISLSLCQREAD | SEQ ID NO: 44 | Rana pipiens | Q8QFQ3 |
| Variant.21 | PMLLLFFLGTISLSLCQEERGA | SEQ ID NO: 45 | Indosylvirana temporalis | ADE40980 |
| Variant.22 | SLLLLFFLGTINLSLCQDETNA | SEQ ID NO: 46 | Odorrana grahami | ABG76537 |
| Variant.23 | SMLLLFFLGTINLSLCEEERDA | SEQ ID NO: 47 | Pelophylax esculentus | P32412 |
| Variant.24 | SMLLLFFLGTISLSLCEEER | SEQ ID NO: 48 | Rana amurensis | AFX61483 |
| Variant.25 | SMLLLFFLGTISLSLCEEERDA | SEQ ID NO: 49 | Rana ornativentris | BAI53086 |
| Variant.26 | SMLLLFFLGTISLSLCEEERSA | SEQ ID NO: 50 | Amolops jingdongensis | AFY06624 |
| Variant.27 | SMLLLFFLGTISLSLCEEERNA | SEQ ID NO: 51 | Amolops loloensis | AFX61483 |
| Variant.28 | SMLLLFFLGTISLSLCEEERGA | SEQ ID NO: 52 | Rana palustris | ANW09708 |
| Variant.29 | SMLLFFFLGTISLSLCQEEERGA | SEQ ID NO: 53 | Rana chensinensis | ALA55867 |
| Variant.30 | SLLLLFFLGTISLSLCEEERNA | SEQ ID NO: 54 | Rana dybowskii | AFP24872 |
| Variant.31 | SMLLIFFLGTISLSLCEQERDA | SEQ ID NO: 55 | Rana draytonii | AFR43679 |

FIG. 7A

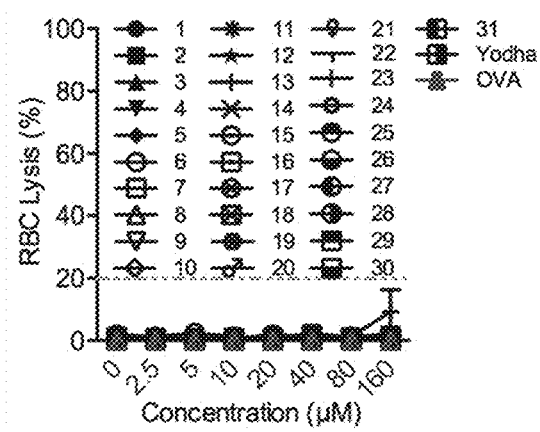

FIG. 7B

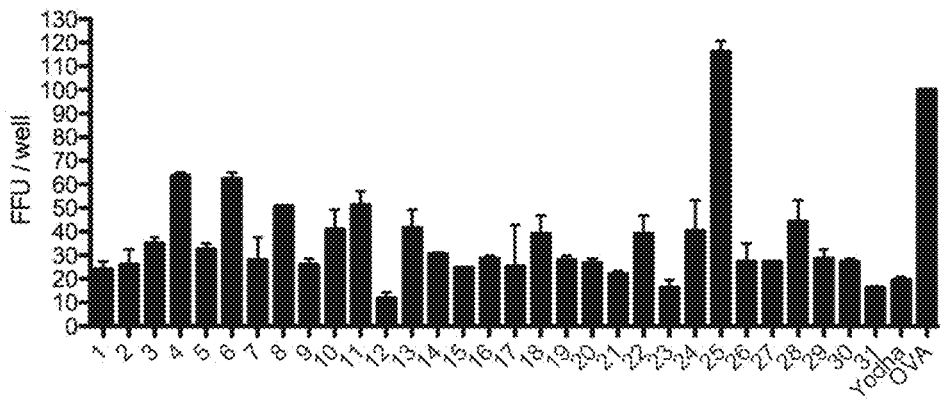
FIG. 7C
| Yodha | SMLLLFFLGTISLSLCQDDQERC | SEQ ID NO: 1 |
| Short Yodha | SMLLLFFLGTISLSLCQ | SEQ ID NO: 56 |
| Short Yodha12 | PMLLLFFLGTISLSLCQ | SEQ ID NO: 57 |
| S1P Yodha | PMLLLFFLGTISLSLCQDDQERC | SEQ ID NO: 58 |
FIG. 7D
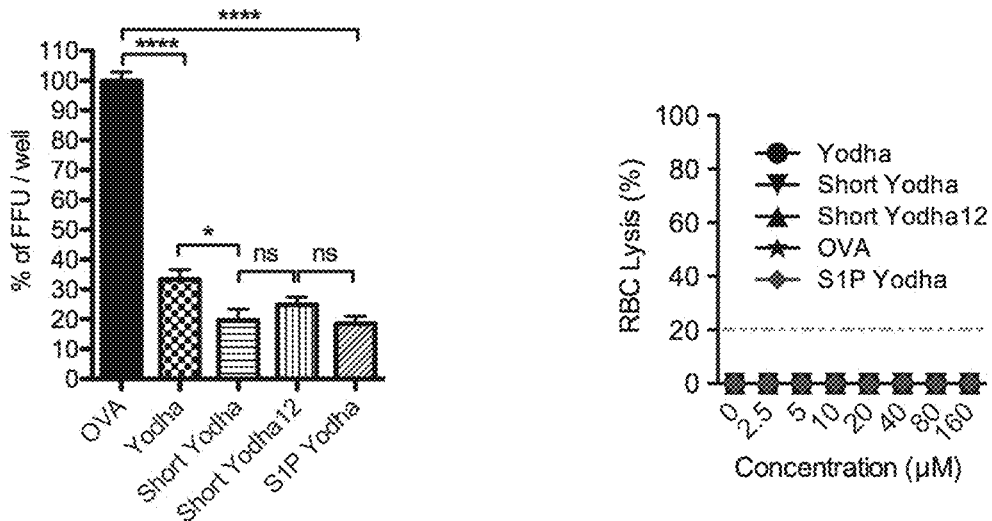
FIG. 7E
FIG. 7F

POLYPEPTIDES FOR MANAGING VIRAL INFECTIONS

CROSS-REFERENCE TO RELATED APPLICATIONS

This is a divisional of U.S. patent application Ser. No. 16/469,119, filed Jun. 12, 2019, which is a § 371 U.S. national stage of International Application No. PCT/US2017/064330, filed Dec. 1, 2017, which claims the benefit of U.S. Provisional Application No. 62/433,490, filed Dec. 13, 2016 and U.S. Provisional Application No. 62/466,066, filed Mar. 2, 2017. The entirety of each of the prior applications is hereby incorporated by reference for all purposes.

STATEMENT REGARDING FEDERALLY FUNDED RESEARCH

This invention was made with government support under R01AI100110, U19AI083019, and R56AI110516 awarded by National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 6975-102541-11_Sequence_Listing.txt. The text file is 22.4 KB, was created on Dec. 18, 2020, and is being submitted electronically via EFS-Web.

BACKGROUND

Zika virus (ZIKV) is a mosquito-borne virus that belongs to the family Flaviviridae and is closely related to West Nile virus (WNV), Dengue virus (DENV), and Japanese Encephalitis virus (JEV) (Gould et al., Lancet 371, 500-509, (2008)). Similar to DENY, ZIKV is spread through the bite of an infected Aedes sp. mosquito (Dick et al. Trans R Soc Trop Med Hyg 46, 509-520 (1952); Shan et al. Cell Host & Microbe 19, 891-900, (2016)). However, unlike other flaviviruses, ZIKV can be vertically transmitted from an infected mother to the developing fetus in utero, resulting in congenital Zika syndrome. Congenital Zika syndrome is characterized by spontaneous abortion, fetal brain abnormalities and microcephaly (Adams Waldorf et al. Nat Med 22, 1256-1259, (2016); Tabata et al. Cell Host Microbe 20, 155-166, (2016); Besnard et al. French Polynesia, Euro Surveill 19 (2014); Mysorekar et al. N Engl J Med 375, 481-484, (2016); Schuler-Faccini et al. MMWR Morb Mortal Wkly Rep 65, 59-62, (2016)). In adults, ZIKV has also been linked to Guillain-Barre syndrome, a disorder in which the immune system attacks the nervous system. Recently, it has been shown that the Brazilian strain of ZIKV causes birth defects in an experimental mouse model (Lazear et al. Cell Host Microbe 19, 720-730, (2016)). Employing this mouse model, a vaccine has been developed that offers complete protection in susceptible mice against ZIKV challenge (Stettler et al. Science 353, 823-826, (2016)). However, there are concerns that the vaccine might promote antibody dependent enhancement, which increases infection susceptibility similar to what is observed in DENV infection (Dejnirattisai et al. Nat Immunol 17, 1102-1108, (2016)). A potential strategy to combat ZIKV infection would be to develop antiviral therapeutics to treat or prevent infection.

Dengue viruses (DENV) are the most prevalent arthropod-borne viral pathogens infecting humans. These mosquito-transmitted viruses are endemic to most tropical and sub-tropical countries with nearly half of the world's population living at risk of DENV infection and resulting in over a million estimated infections annually (Mackenzie et al. Nat Med 10, S98-109, (2004)). Infection with DENV can cause a broad range of symptoms, ranging from subclinical, to the self-limiting flu-like illness dengue fever (DF), to the more severe and life-threatening dengue hemorrhagic fever and shock syndrome (DHF/DSS) characterized by increased vascular permeability producing plasma leakage, severe thrombocytopenia and hypotension leading to circulatory collapse (Gubler, *Novartis Found Symp* 277, 3-16, (2006)). DENV prevalence, infection rates, and disease severity have increased exponentially since the middle of the last century (Guzman et al. *Nat Rev Microbiol* 8, S7-S16, (2010)). Despite decades of interest, need, and effort there remains no available dengue vaccine and vaccine candidates continue to run into roadblocks and safety concerns both in pre-clinical development and in clinical trials.

Influenza is a public health concern as it results in economic burden, morbidity and even mortality. Influenza infection may result in a variety of disease states, ranging from sub-clinical infection through a mild upper respiratory infection and tracheobronchitis to a severe occasionally lethal viral pneumonia. The reasons for this wide spectrum of severity are explained by the site of infection and the immune status of the host. The most important characteristic of influenza, from the immunological point of view, is the rapid, unpredictable changes of the surface glycoproteins, haemagglutinin and neuraminidase, referred to as antigenic shifts and drifts. These changes lead eventually to the emergence of new influenza strains, which enable the virus to escape the immune system and are the cause for almost annual epidemics (Laver et al., Nature 283, 454-457 (1980); Laver et al., *Philosophical Trans. Royal Soc. B,* 288(1029), 313-326, (1980)). Immunization towards influenza virus is limited by this marked antigenic variation of the virus and by the restriction of the infection to the respiratory mucous membranes. The influenza vaccines currently available and licensed are based either on whole inactive virus, or on viral surface glycoproteins. These influenza vaccines fail to induce complete, long-term and cross-strain immunity.

There is thus a need for improved compositions and methods to protect against viral pathogens. The compositions and methods described herein address these and other needs.

SUMMARY

In accordance with the purposes of the disclosed materials, compounds, compositions, kits and methods, as embodied and broadly described herein, the disclosed subject matter relates to compounds, compositions, methods of making said compounds and/or compositions, and methods of using said compounds and/or compositions.

More specifically, disclosed herein are isolated peptides and compositions comprising polypeptides, variants, the derivatives thereof having antiviral activity. In some embodiments, the polypeptides comprise an amino acid sequence comprising or consisting of at least 60% identity to an amino acid sequence disclosed herein such as those selected from SEQ ID NO: 1-58 and SEQ ID NO: 59-77, e.g., a peptide selected from the group consisting of SEQ ID NO:1, SEQ ID NO:36, SEQ ID NO:56, SEQ ID NO:57, SEQ ID NO:58, and SEQ ID NO: 65. For example, the composition can comprise or consist of a polypeptide having the amino acid sequence SEQ ID NO:1 or an amino acid sequence having at least 60% sequence identity to SEQ ID NO:1. In other examples, the composition can comprise or consist of a polypeptide having the amino acid sequence SEQ ID NO:36 or an amino acid sequence having at least 60% sequence identity to SEQ ID NO:36. In still other examples, the composition can comprise or consist of a polypeptide having the amino acid sequence SEQ ID NO:56 or an amino acid sequence having at least 80% sequence identity to SEQ ID NO:56. In further examples, the composition can comprise or consist of a polypeptide having the amino acid sequence SEQ ID NO:57 or an amino acid sequence having at least 80% sequence identity to SEQ ID NO:57. In still further examples, the composition can comprise or consist of a polypeptide having the amino acid sequence SEQ ID NO:58 or an amino acid sequence having at least 60% sequence identity to SEQ ID NO:58. In still further examples, the composition can comprise or consist of a polypeptide having the amino acid sequence SEQ ID NO: 65 or an amino acid sequence having at least 60% sequence identity to SEQ ID NO: 65. In some embodiments, the polypeptides in the compositions can include at least one modification such as amidation or acetylation.

In some embodiments, the polypeptides comprise an amino acid sequence comprising or consisting of at least 60% identity to an amino acid sequence disclosed herein, e.g., selected from the group consisting of SEQ ID NO: 1-58, or 59-77 or having LFFX$^1$GTIX$^2$LX$^3$LC (SEQ ID NO: 78); wherein X$^1$ is any amino acid; X$^2$ is any amino acid or S or N; and X$^3$ is any amino acid, in certain embodiments, X$^1$ is L, A, any amino acid, or any amino acid but not L; and X$^3$ is S, A, any amino acid, or any amino acid but not S. In certain embodiments, the polypeptide is not greater than 18, 20, 22, 25, 27, 30, 35, or 40 amino acids.

In some embodiments, the polypeptides comprise an amino acid sequence comprising or consisting of at least 60% identity to an amino acid sequence disclosed herein, e.g., selected from the group consisting of SEQ ID NO: 1-58, or 59-77 or having LFFX$^1$GTIX$^2$LX$^3$LCX$^4$DD (SEQ ID NO: 79); wherein X$^1$ is any amino acid; X$^2$ is any amino acid, X$^3$ is any amino acid and X$^4$ is any amino acid. In certain embodiments, X$^1$ is L, A, any amino acid, or any amino acid but not L; X$^2$ is S or N; and X$^3$ is S, A, any amino acid, or any amino acid but not S; and X$^4$ is Q, E, A, or any amino acid. In certain embodiments, the polypeptide is not greater than 18, 20, 22, 25, 27, 30, 35, or 40 amino acids.

In some embodiments, the polypeptides comprise an amino acid sequence comprising or consisting of at least 60% identity to an amino acid sequence disclosed herein, e.g., selected from the group consisting of SEQ ID NO: 1-58, or 59-77 or having LFFX$^1$GTIX$^2$LX$^3$LCX$^4$DDQERC (SEQ ID NO: 80); wherein X$^1$ is any amino acid; X$^2$ is any amino acid, X$^3$ is any amino acid and X$^4$ is any amino acid. In certain embodiments, X$^1$ is L, A, any amino acid, or any amino acid but not L; X$^2$ is S or N; and X$^3$ is S, A, any amino acid, or any amino acid but not S; and X$^4$ is Q, E, A, or any amino acid. In certain embodiments, the polypeptide is not greater than 18, 20, 22, 25, 27, 30, 35, or 40 amino acids.

In some embodiments, the disclosure relates to compositions, comprising: a polypeptide comprising an amino acid sequence having at least 60% identity to an amino acid sequence disclosed herein or derivatives or prodrugs thereof and a pharmaceutically acceptable carrier.

In certain embodiments, the disclosure relates to recombinant vectors comprising a nucleic acid encoding peptide disclosed herein. In certain embodiments, the disclosure relates to expression systems comprising a recombinant vector comprising a nucleic acid encoding peptide disclosed herein. In certain embodiments, the disclosure relates to cells comprising a recombinant vector comprising a nucleic acid encoding peptide disclosed herein. In certain embodiments, the disclosure relates to a vector comprising the nucleic acid encoding a peptide disclosed herein and a heterologous nucleic acid sequence. In certain embodiments, the disclosure relates to a vector comprising the nucleic acid encoding a peptide disclosed herein in operable combination with a heterologous promoter sequence.

In certain embodiments, the disclosure relates to a nucleic acid encoding a polypeptide disclosed herein wherein the nucleotide sequence has been changed to contain at least one non-naturally occurring substitution and/or modification relative to the naturally occurring sequence, e.g., one or more nucleotides have been changed relative to the natural sequence. In certain embodiments, the disclosure relates to a nucleic acid encoding a polypeptide disclosed herein further comprising a label. In certain embodiments, the nucleic acid comprises a sequence that encodes a peptide disclosed herein in operable combination with a heterologous promoter.

In certain embodiments, the disclosure relates to pharmaceutical compositions comprising a peptide disclosed herein and a pharmaceutically acceptable excipient. In certain embodiments, the pharmaceutical composition is in the form of a capsule, tablets, pill, powder, granule, or gel. In certain embodiments, the pharmaceutical composition is in the form of a sterilized pH buffered aqueous salt solution, or in the form of a container configured to spray a liquid, or in the form of a sealed container with a propellant. In certain embodiments, the disclosure contemplates the preparation of a medicament disclosed herein for useful for treating or preventing viral infections. In certain embodiments, the pharmaceutical compositions is in solid form surrounded by an enteric coating. In certain embodiments, the pharmaceutical compositions a pharmaceutically acceptable excipient is a solubilizing agent.

The compositions can further include a pharmaceutically acceptable carrier. In some embodiments, the compositions can be in the form of a vaccine. The vaccine can further include a pharmaceutically acceptable adjuvant.

Methods of using the compositions are also disclosed herein. The compositions can be used for preventing or treating a viral infection such as influenza, HIV, Zika or dengue infection. The methods disclosed herein can include administering to the subject a composition comprising a polypeptide as described herein. In some embodiments, the method can further include administering at least one additional antiviral compound to the subject.

In certain embodiments, this disclosure relates to method for preventing or treating a viral infection in a subject in need thereof, the method comprising administering to the subject an effective amount a polypeptide disclosed herein derivatives, or prodrugs thereof. In certain embodiments, the viral infection is a Zika virus. In certain embodiments, the viral infection is a dengue virus. In certain embodiments, the viral infection is an influenza virus. In certain embodiments, the viral infection is human immunodeficiency virus (HIV), a lentivirus, or a retrovirus virus.

In certain embodiments, the polypeptide is administered in combination with a nucleoside reverse transcriptase inhibitor, non-nucleoside reverse transcriptase inhibitor, a protease inhibitor, fusion or cell entry inhibitor, an integrase inhibitor, CYP3A inhibitor, or combinations thereof.

In certain embodiments, the combination is selected from a combination of: abacavir and lamivudine; abacavir, dolutegravir, and lamivudine; abacavir, lamivudine, and zidovudine; atazanavir and cobicistat; darunavir and cobicistat; dolutegravir and rilpivirine; efavirenz, emtricitabine, and tenofovir disoproxil fumarate; elvitegravir, cobicistat, emtricitabine, and tenofovir alafenamide fumarate; elvitegravir, cobicistat, emtricitabine, and tenofovir disoproxil fumarate; emtricitabine, rilpivirine, and tenofovir alafenamide; emtricitabine, rilpivirine, and tenofovir disoproxil fumarate; emtricitabine and tenofovir alafenamide; emtricitabine and tenofovir disoproxil fumarate; lamivudine and zidovudine; and lopinavir and ritonavir.

In certain embodiments, this discourse relates to the production of a medicament comprising peptides, variants, and derivatives disclosed herein and compositions with the same for use in the treatment or prevention of a viral infection.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

FIG. 6A. Lists alanine-scanning mutants of Yodha peptide (SEQ ID NO: 1-24).

FIG. 6B. Shows change in virucidal activity of alanine-scanning mutant peptides compared with Yodha peptide, which was set as zero. T-test two tailed p-value (*) p=0.021, (ns) non-significant p=0.1553.

FIG. 6C. Shows each of the alanine scan mutants tested for cytotoxicity using human red blood cells.

FIG. 6D. Shows data showing both L and D amino acids are effective for Zika.

FIG. 7A. Shows naturally-occurring variants of Yodha peptides inhibit ZIKV—list of natural variants of the Yodha peptide (SEQ ID NO: 1, 25-55).

FIG. 7B. Shows cytotoxicity tests, which show that the Yodha peptide variants are non-toxic to human RBCs.

FIG. 7C. Shows each of these naturally occurring variants of Yodha peptide was tested for their ability to neutralize ZIKV. All variants except one inhibited ZIKV.

FIG. 7D. Shows truncated and mutant Yodha peptides tested (SEQ ID NO: 56-58).

FIG. 7E. Shows ability of mutant peptides to inhibit ZIKV.

FIG. 7F. Shows the lack of toxicity.

DETAILED DESCRIPTION

Figure 1A:
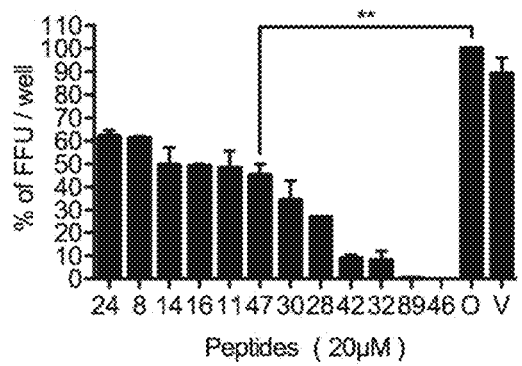
FIG. 1A. Data in screening and identification of frog peptides against Zika virus. Host defense peptides were incubated with ZIKV for two hours and virus viability was tested using focus-forming assay (FFA) of ZIKV at 72 hours post infection. OVA peptide used as a negative control (set as a 100% of FFU/well). T-test, Two-tailed p value p=0.0077 (**).

The materials, compounds, compositions, kits and methods described herein may be understood more readily by reference to the following detailed description of specific aspects of the disclosed subject matter and the Examples and Figures included therein. Before the present materials, compounds, compositions, kits and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Definitions

In this specification and in the claims that follow, reference will be made to a number of terms that shall be defined to have the following meanings:

It must be noted that as used herein and in the appended claims, the singular forms "a," "an," and "the" include plural referents unless the context clearly dictates otherwise.

The term "comprising" in reference to a peptide having an amino acid sequence refers a peptide that may contain additional N-terminal (amine end) or C-terminal (carboxylic acid end) amino acids, i.e., the term is intended to include the amino acid sequence within a larger peptide.

The term "consisting of" in reference to a peptide having an amino acid sequence refers a peptide having the exact number of amino acids in the sequence and not more or having not more than a rage of amino acids expressly specified in the claim.

"Optional" or "optionally" means that the subsequently described event or circumstance can or cannot occur, and that the description includes instances where the event or circumstance occurs and instances where it does not. For example, the phrase "optionally an adjuvant" means that the adjuvant may or may not be included.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "amidation" refers to the conversion of a carboxylic acid to an amide, e.g., at the C-terminus of a polypeptide.

The term "acetylation" refers to the substitution of an amine group with an acetyl group, e.g. at the N-terminus of a polypeptide.

The term "variant" refers to an amino acid sequence having amino acid insertions, deletions, conservative or non-conservative substitutions, or a peptide having 60%, 65%, 70%, 71%, 72%, 73%, 74%, 75%, 76%, 77%, 78%, 79%, 80%, 81%, 82%$, 83%, 84%, 85%, 86%, 87%, 88%, 89%, 90%, 91%, 92%, 93%, 94%, 95%, 96%, 97%, 98%, or 99% sequence homology or identify to the recited sequence.

Variants include allelic variants. The term "allelic variant" refers to a polypeptide containing polymorphisms that lead to changes in the amino acid sequences of a peptide and that exist within a natural population (e.g., a frog species or variety). Such natural allelic variations can typically result in 1-5% variance in a polypeptide. Allelic variants can be identified by sequencing the polypeptide sequence of interest in a number of different species, which can be readily carried out by using hybridization probes to identify the same genetic locus in those species. Any and all such resulting amino acid polymorphisms or variations that are the result of natural allelic variation and that do not alter the functional activity of peptide of interest, are intended to be within the scope of the disclosure.

The term "vaccine" as used herein refers to a composition that provides immunity to an individual upon challenge.

The terms "antiviral" and "virucidal" are used interchangeably and refer to an agent that is capable of inhibiting and/or killing viral particles and/or preventing an infection caused viral particles.

The term "inhibit" refers to a decrease in an activity, response, condition, disease, or other biological parameter. This can include but is not limited to the complete ablation of the activity, response, condition, or disease. This can also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

By "reduce" or other forms of the word, such as "reducing" or "reduction," is meant lowering of an event or characteristic (e.g., viral infection). It is understood that this is typically in relation to some standard or expected value, in other words it is relative, but that it is not always necessary for the standard or relative value to be referred to. For example, "reduces viral infection" means reducing the rate of infection of a virus relative to a standard or a control.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

As used herein, the term "sterilized" refers to subjecting something to a process that effectively kills or eliminates transmissible agents (such as fungi, bacteria, viruses, prions and spore forms etc.). Sterilization can be achieved through application of heat, chemicals, irradiation, high pressure or filtration. One process involves water prepared by distillation and stored in an airtight container wherein suitable additives are introduced to approximate isotonicity.

The term "polynucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The polynucleotide may be generated in any manner, including chemical synthesis, DNA replication, reverse transcription, or a combination thereof. The term "oligonucleotide" generally refers to a short length of single-stranded polynucleotide chain usually less than 30 nucleotides long, although it may also be used interchangeably with the term "polynucleotide."

The term "nucleic acid" refers to a polymer of nucleotides, or a polynucleotide, as described above. The term is used to designate a single molecule, or a collection of molecules. Nucleic acids may be single stranded or double stranded, and may include coding regions and regions of various control elements.

A "heterologous" nucleic acid sequence or peptide sequence refers to a nucleic acid sequence or peptide sequence that do not naturally occur, e.g., because the whole sequences contain a segment from other plants, bacteria, viruses, other organisms, or joinder of two sequences that occur the same organism but are joined together in a manner that does not naturally occur in the same organism or any natural state.

The term "recombinant" when made in reference to a nucleic acid molecule refers to a nucleic acid molecule which is comprised of segments of nucleic acid joined together by means of molecular biological techniques provided that the entire nucleic acid sequence does not occurring in nature, i.e., there is at least one mutation in the overall sequence such that the entire sequence is not naturally occurring even though separately segments may occurring in nature. The segments may be joined in an altered arrangement such that the entire nucleic acid sequence from start to finish does not naturally occur. The term "recombinant" when made in reference to a protein or a polypeptide refers to a protein molecule that is expressed using a recombinant nucleic acid molecule.

The terms "protein," "peptide," and "polypeptide" are used interchangeably to refer to compounds comprising amino acids joined via peptide bonds and are used interchangeably. Amino acids may be naturally or non-naturally occurring. A "chimeric protein" or "fusion protein" is a molecule in which different portions of the protein are derived from different origins such that the entire molecule is not naturally occurring. A chimeric protein may contain amino acid sequences from the same species of different species as long as they are not arranged together in the same way that they exist in a natural state. Examples of a chimeric protein include sequences disclosed herein that are contain one, two or more amino acids attached to the C-terminal or N-terminal end that are not identical to any naturally occurring protein, such as in the case of adding an amino acid containing an amine side chain group, e.g., lysine, an amino acid containing a carboxylic acid side chain group such as aspartic acid or glutamic acid, a polyhistidine tag, e.g. typically four or more histidine amino acids. Contemplated chimeric proteins include those with self-cleaving peptides such as P2A-GSG. See Wang. Scientific Reports 5, Article number: 16273 (2015).

As used herein, the term "derivative" refers to a structurally similar peptide that retains sufficient functional attributes of the identified analogue. The derivative may be structurally similar because it is lacking one or more atoms, e.g., replacing an amino group, hydroxyl, or thiol group with a hydrogen, substituted, a salt, in different hydration/oxidation states, or because one or more atoms within the molecule are switched, such as, but not limited to, replacing a oxygen atom with a sulfur atom or replacing an amino group with a hydroxyl group. The derivative may be a prodrug, comprise a lipid, polyethylene glycol, saccharide, polysaccharide. A derivative may be two or more peptides linked together by a linking group. It is contemplated that the linking group may be biodegradable. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

In certain embodiments, the peptides discloses herein have at least one non-naturally occurring molecular modification, such as the attachment of polyethylene glycol, the attachment of a chimeric peptide, the attachment of a fluorescent dye comprising aromatic groups, fluorescent peptide, a chelating agent capable of binding a radionuclide such as $^{18}F$, N-terminal acetyl, propionyl group, myristoyl and palmitoyl, group or N-terminal methylation, or a C-terminal alkyl ester. In certain embodiments, the disclosure contemplates the disclosure contemplates peptides disclosed herein labeled using commercially available biotinylation reagents. Biotinylated peptide can be used in streptavidin affinity binding, purification, and detection. In certain embodiments, the disclosure contemplates peptide disclose herein containing azide-derivatives of naturally occurring monosaccharides such as N-azidoacetylglucosamine, N-azidoacetylmannosamine, and N-azido acetylg alacto s amine.

In certain embodiments, this disclosure contemplates derivatives of peptide disclose herein wherein one or more amino acids are substituted with chemical groups to improve pharmacokinetic properties such as solubility and serum half-life, optionally connected through a linker. In certain embodiments, such a derivative may be a prodrug wherein the substituent or linker is biodegradable, or the substituent or linker is not biodegradable. In certain embodiments, contemplated substituents include a saccharide, polysaccharide, acetyl, fatty acid, lipid, and/or polyethylene glycol. The substituent may be covalently bonded through the formation of amide bonds on the C-terminus or N-terminus of the peptide optionally connected through a linker. In certain embodiments, it is contemplated that the substituent may be covalently bonded through an amino acid within the peptide, e.g. through an amine side chain group such as lysine or an amino acid containing a carboxylic acid side chain group such as aspartic acid or glutamic acid, within the peptide comprising a sequence disclosed herein. In certain embodiments, it is contemplated that the substituent may be covalently bonded through a cysteine in a sequence disclosed herein optionally connected through a linker. In certain embodiments, a substituent is connected through a linker that forms a disulfide with a cysteine amino acid side group.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO$_2$Rb, —C(=O)Ra, —C(=O)ORa, —C(=O)NRaRb, —OC(=O)NRaRb, —ORa, —SRa, —SORa, —S(=O)$_2$Ra, —OS(=O)$_2$Ra and —S(=O)$_2$ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, and heteroarylalkyl. The substituents may further optionally be substituted.

As used herein, a "lipid" group refers to a hydrophobic group that is naturally or non-naturally occurring that is highly insoluble in water. As used herein a lipid group is considered highly insoluble in water when the point of connection on the lipid is replaced with a hydrogen and the resulting compound has a solubility of less than $0.63 \times 10^{-4}$% w/w (at 25° C.) in water, which is the percent solubility of octane in water by weight. See Solvent Recovery Handbook, 2$^{nd}$ Ed, Smallwood, 2002 by Blackwell Science, page 195. Examples of naturally occurring lipids include saturated or unsaturated hydrocarbon chains found in fatty acids, glycerolipids, cholesterol, steroids, polyketides, and derivatives. Non-naturally occurring lipids include derivatives of naturally occurring lipids, acrylic polymers, aromatic, and alkylated compounds and derivatives thereof.

The term "prodrug" refers to an agent that is converted into a biologically active form in vivo. Prodrugs are often useful because, in some situations, they may be easier to administer than the parent compound. The prodrug may also have improved solubility in pharmaceutical compositions over the parent drug. A prodrug may be converted into the parent drug by various mechanisms, including enzymatic processes and metabolic hydrolysis. Typical prodrugs are pharmaceutically acceptable esters. Prodrugs include compounds wherein a hydroxy, amino or mercapto (thiol) group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

For example, if a disclosed peptide or a pharmaceutically acceptable form of the peptide contains a carboxylic acid functional group, a prodrug can comprise a pharmaceutically acceptable ester formed by the replacement of the hydrogen atom of the acid group with a group such as ($C_1$-$C_8$)alkyl, ($C_2$-$C_{12}$)alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N-($C_1$-$C_2$)alkylamino($C_2$-$C_3$)alkyl (such as beta-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

If a disclosed peptide or a pharmaceutically acceptable form of the peptide contains an alcohol functional group, a prodrug can be formed by the replacement of the hydrogen atom of the alcohol group with a group such as ($C_1$-$C_6$) alkanoyloxymethyl, 1-(($C_1$-$C_6$)alkanoyloxy) ethyl, 1-methyl-1(($C_1$-$C_6$)alkanoyloxy)ethyl ($C_1$-$C_6$)alkoxycarbonyloxymethyl, —N-($C_1$-$C_6$)alkoxycarbonylaminomethyl, succinoyl, ($C_1$-$C_6$)alkanoyl, alpha-amino($C_1$-$C_4$)alkanoyl, arylacyl and alpha-aminoacyl, or alpha-aminoacyl-alpha-aminoacyl, where each alpha-aminoacyl group is independently selected from naturally occurring L-amino acids P(O)(OH)$_2$, —P(O)(O($C_1$-$C_6$)alkyl)$_2$, and glycosyl (the radical resulting from the removal of a hydroxyl group of the hemiacetal form of a carbohydrate).

If a disclosed peptide or a pharmaceutically acceptable form of the peptide incorporates an amine functional group, a prodrug can be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, a natural alpha-aminoacyl, —C(OH)C(O)OY$_1$ wherein Y$^1$ is H, ($C_1$-$C_6$)alkyl or benzyl, —C(OY$_2$)Y$_3$ wherein Y$_2$ is ($C_1$-$C_4$) alkyl and Y$_3$ is ($C_1$-$C_6$)alkyl, carboxy($C_1$-$C_6$)alkyl, amino($C_1$-$C_4$)alkyl or mono-Nor di-N,N-($C_1$-$C_6$)alkylaminoalkyl, —C(Y$_4$)Y$_5$ wherein Y$_4$ is H or methyl and Y$_5$ is mono-N- or di-N,N-($C_1$-$C_6$)alkylamino, morpholino, piperidin-1-yl or pyrrolidin-1-yl.

As used herein, "pharmaceutically acceptable esters" include, but are not limited to, alkyl, alkenyl, alkynyl, aryl, arylalkyl, and cycloalkyl esters of acidic groups, including, but not limited to, carboxylic acids, phosphoric acids, phosphinic acids, sulfonic acids, sulfinic acids, and boronic acids.

As used herein, "pharmaceutically acceptable enol ethers" include, but are not limited to, derivatives of formula —C=C(OR) where R can be selected from alkyl, alkenyl, alkynyl, aryl, aralkyl, and cycloalkyl. Pharmaceutically acceptable enol esters include, but are not limited to, derivatives of formula —C=C(OC(O)R) where R can be selected from hydrogen, alkyl, alkenyl, alkynyl, aryl, aralkyl, and cycloalkyl.

A "linking group" refers to any variety of molecular arrangements that can be used to bridge to molecular moieties together. An example formula may be —$R_m$— wherein R is selected individually and independently at each occurrence as: —$CR_mR_m$—, —CHRm—, —CH—, —C—, —$CH_2$—, —C(OH)$R_m$, —C(OH)(OH)—, —C(OH)H, —C(Hal)$R_m$—, —C(Hal)(Hal)—, —C(Hal)H—, —C($N_3$)$R_m$—, —C(CN)$R_m$, —C(CN)(CN)—, —C(CN)H—, —C($N_3$)($N_3$)—, —C($N_3$)H—, —O—, —S—, —N—, —NH—, —$NR_m$—, —(C=O)—, —(C=NH)—, —(C=S)—, —(C=$CH_2$)—, which may contain single, double, or triple bonds individually and independently between the R groups. If an R is branched with an $R_m$ it may be terminated with a group such as —$CH_3$, —H, —CH=$CH_2$, —CCH, —OH, —SH, —NH2, —$N_3$, —CN, or —Hal, or two branched Rs may form a cyclic structure. It is contemplated that in certain instances, the total Rs or "m" may be less than 100, or 50, or 25, or 10. Examples of linking groups include bridging alkyl groups and alkoxyalkyl groups. Linking groups may be substituted with one or more substituents.

As used herein, the term "biodegradable" in reference to a substituent or linker refers to a molecular arrangement in a peptide derivative that when administered to a subject, e.g., human, will be broken down by biological mechanism such that a metabolite will be formed and the molecular arrangement will not persist for over a long period of time, e.g., the molecular arrangement will be broken down by the body after a several hours or days. In certain embodiments, the disclosure contemplates that the biodegradable linker or substituent will not exist after a week or a month.

"Subject" to which administration is contemplated includes, but is not limited to, humans (e.g., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

In certain embodiments, term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity.

In certain embodiments, sequence "identity" refers to the number of exactly matching amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example, the polypeptides GGGGG and GGGGT have a sequence identity of 4 out of 5 or 80%. For example, the polypeptides GGGPPP and GGGAPPP have a sequence identity of 6 out of 7 or 85%. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic—A V I L; Charged positive: R K H; Charged negative—D E; Polar—S T N Q. The amino acid groups are also considered conserved substitutions.

The terms "a nucleic acid sequence encoding" a specified polypeptide refers to a nucleic acid sequence comprising the coding region of a gene or in other words the nucleic acid sequence, which encodes a gene product. The coding region may be present in either a cDNA, genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

In contrast, a "regulatable" or "inducible" promoter is one which is capable of directing a level of transcription of an operably linked nuclei acid sequence in the presence of a stimulus (e.g., heat shock, chemicals, light, etc.) which is different from the level of transcription of the operably linked nucleic acid sequence in the absence of the stimulus.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species, or from different species.

Reference will now be made in detail to specific aspects of the disclosed materials, compounds, compositions, articles, and methods, examples of which are illustrated in the accompanying Examples and Figures.

Polypeptides

In certain embodiments, this disclosure relates to a polypeptides disclosed herein and variants thereof, such as any of the peptides comprising or consisting or SEQ ID NO: 1-77. In certain embodiments, the peptide comprising amino acid sequence LFFX$^1$GTIX$^2$LX$^3$LC (SEQ ID NO: 78); wherein X$^1$ is any amino acid; X$^2$ is S or N; and X$^3$ is any amino acid, in certain embodiments, X$^1$ is L, A, any amino acid, or any amino acid but not L; and X$^3$ is S, A, any amino acid, or any amino acid but not S.

In certain embodiments, the polypeptide consists of the amino acid sequence SMLLLFFLGTISLSLCQDDQERC (SEQ ID NO: 1). In certain embodiments, the polypeptide consist of the amino acid sequence. SMLLLFFLGTIS-LSLCQ (SEQ ID NO:56), or PMLLLFFLGTISLSLCQ (SEQ ID NO:57). In certain embodiments, the polypeptide consist of the amino acid sequence LLFFLGTIS-LSLCQDDQERC (SEQ ID NO: 65). In certain embodiments, the polypeptide has one or two amino acid substitutions.

In certain embodiments, the polypeptide comprising an amino acid sequence comprising LFFX$^1$GTIX$^2$LX$^3$LC (SEQ ID NO: 78); wherein X$^1$ is any amino acid; X$^2$ is any amino acid or S or N; and X$^3$ is any amino acid. In certain embodiments, X$^1$ is A or any other amino acid but not L. In certain embodiments, X$^3$ is A or any other amino acid but not S.

In some embodiments, the polypeptides comprise an amino acid sequence comprising or consisting of at least 60% identity to an amino acid sequence disclosed herein, e.g., selected from the group consisting of SEQ ID NO: 1-58, or 59-77 or having LFFX$^1$GTIX$^2$LX$^3$LC (SEQ ID NO: 78); wherein X$^1$ is any amino acid; X$^2$ is any amino acid or S or N; and X$^3$ is any amino acid, in certain embodiments, X$^1$ is L, A, any amino acid, or any amino acid but not L; and X$^3$ is S, A, any amino acid, or any amino acid but not S. In certain embodiments, the polypeptide is not greater than 18, 20, 22, 25, 27, 30, 35, or 40 amino acids.

In some embodiments, the polypeptides comprise an amino acid sequence comprising or consisting of at least 60% identity to an amino acid sequence disclosed herein, e.g., selected from the group consisting of SEQ ID NO: 1-58, or 59-77 or having LFFX$^1$GTIX$^2$LX$^3$LCX$^4$DD (SEQ ID NO: 79); wherein X$^1$ is any amino acid; X$^2$ is any amino acid, X$^3$ is any amino acid and X$^4$ is any amino acid. In certain embodiments, X$^1$ is L, A, any amino acid, or any amino acid but not L; X$^2$ is S or N; and X$^3$ is S, A, any amino acid, or any amino acid but not S; and X$^4$ is Q, E, A, or any amino acid. In certain embodiments, the polypeptide is not greater than 18, 20, 22, 25, 27, 30, 35, or 40 amino acids.

In some embodiments, the polypeptides comprise an amino acid sequence comprising or consisting of at least 60% identity to an amino acid sequence disclosed herein, e.g., selected from the group consisting of SEQ ID NO: 1-58, or 59-77 or having LFFX$^1$GTIX$^2$LX$^3$LCX$^4$DDQERC (SEQ ID NO: 80); wherein X$^1$ is any amino acid; X$^2$ is any amino acid, X$^3$ is any amino acid and X$^4$ is any amino acid. In certain embodiments, X$^1$ is L, A, any amino acid, or any amino acid but not L; X$^2$ is S or N; and X$^3$ is S, A, any amino acid, or any amino acid but not S; and X$^4$ is Q, E, A, or any amino acid. In certain embodiments, the polypeptide is not greater than 18, 20, 22, 25, 27, 30, 35, or 40 amino acids.

Host defense peptides constitute an ancient arm of the innate immune system. They comprise a diverse class of naturally-produced peptides that serve as the first line of defense in all living, uni- and multi-cellular organisms. They neutralize pathogens by either killing them directly by physically disrupting the outer membrane or by blocking internal functions (Zhang et al. Curr Biol 26, R14-R19 (2016)). Host defense peptides from the skin of the forest frogs Hydrophylax bahuvistara and Hylarana aurantiaca found in the Western Ghats of southwestern India have been previously isolated (Vineeth Kumar et al. Acta Biol Hung 67, 121-124, (2016)).

Disclosed herein is a host defense peptide isolated from Hylarana aurantiaca that has been found to have antiviral activity. This peptide is referred to as Yodha peptide and variants have been prepared and are also disclosed herein. Thus, disclosed herein are active fragments and variants of Yodha peptide, which are referred to as polypeptides. The term "polypeptide" is intended to contemplates variants generated by deletion, addition, mutation, substitution, truncation, reversal, or shuffling to the disclosed Yodha peptide sequence, so long as the polypeptide functions to produce an antiviral response as described herein.

The disclosed peptides comprise amino acids coupled by a peptide bond. Each amino acid can be a natural or non-natural amino acid. The term "non-natural amino acid" refers to an organic compound that is a congener of a natural amino acid in that it has a structure similar to a natural amino acid so that it mimics the structure and reactivity of a natural amino acid. The non-natural amino acid can be a modified amino acid, and/or amino acid analog, that is not one of the 20 common naturally occurring amino acids or the rare natural amino acids selenocysteine or pyrrolysine. Non-natural amino acids can also be the D-isomer of the natural amino acids. Examples of suitable amino acids include, but are not limited to, alanine, allosoleucine, arginine, asparagine, aspartic acid, cysteine, glutamine, glutamic acid, glycine, histidine, isoleucine, leucine, lysine, methionine, napthylalanine, phenylalanine, proline, pyroglutamic acid, serine, threonine, tryptophan, tyrosine, valine, a derivative, or combinations thereof. These, and others, are listed in the Table 1 along with their abbreviations used herein.

TABLE 1

Amino Acid Abbreviations

| Amino Acid | Abbreviations* |
|---|---|
| alanine | Ala (A) |
| allosoleucine | AIle |
| arginine | Arg (R) |
| asparagine | Asn (N) |
| aspartic acid | Asp (D) |
| cysteine | Cys (C) |
| cyclohexylalanine | Cha |
| 2,3-diaminopropionic acid | Dap |
| 4-fluorophenylalanine | Fpa (Σ) |
| glutamic acid | Glu (E) |
| glutamine | Gln (Q) |
| glycine | Gly (G) |
| histidine | His (H) |
| homoproline | Pip (Θ) |
| isoleucine | Ile (I) |
| leucine | Leu (L) |
| lysine | Lys (K) |
| methionine | Met (M) |
| napthylalanine | Nal (Φ) |
| norleucine | Nle (Ω) |
| phenylalanine | Phe (F) |
| phenylglycine | Phg (Ψ) |
| 4-(phosphonodifluoromethyl)phenylalanine | F$_2$Pmp (Λ) |
| pipecolic acid | Pp (ϑ) |
| proline | Pro (P) |
| sarcosine | Sar (Ξ) |
| selenocysteine | Sec (U) |
| serine | Ser (S) |
| threonine | Thr (T) |
| tyrosine | Tyr (Y) |
| tryptophan | Trp (W) |
| valine | Val (V) |

*single letter abbreviations: when shown in capital letters herein it indicates the L-amino acid form, when shown in lower case herein it indicates the D-amino acid form Also disclosed are variants of the disclosed polypeptides. Variants are well understood to those of skill in the art and can involve amino acid sequence modifications. For example, amino acid sequence modifications typically fall into one or more of three classes: substitutional, insertional, or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of 1 to 3 residues. Deletions are characterized by the removal of one or more amino acid residues from the peptide sequence. Typically, no more than from 1 to 3 residues are deleted at any one site within the peptide. Amino acid substitutions are typically of single residues, but can occur at a number of different locations at once; insertions usually will be on the order of about from 1 to 3 amino acid residues; and deletions will range about from 1 to 3 residues. Deletions or insertions preferably are made in adjacent pairs, i.e. a deletion of 2 residues or insertion of 2 residues. Substitutions, deletions, insertions or any combination thereof can be combined to arrive at a final construct. Substitutional variants are those in which at least one residue has been removed and a different residue inserted in its place. Such substitutions generally are made in accordance with the following Table 2 and are referred to as conservative substitutions.

TABLE 2

Amino Acid Substitutions
Exemplary Conservative Substitutions

| | |
|---|---|
| Ala replaced by ser | Leu replaced by ile or val |
| Arg replaced by lys or gln | Lys replaced by arg or gln |
| Asn replaced by gln or his | Met replaced by leu or ile |

TABLE 2-continued

Amino Acid Substitutions
Exemplary Conservative Substitutions

| | |
|---|---|
| Asp replaced by glu | Phe replaced by met, leu, tyr, or fpa |
| Cys replaced by ser | Ser replaced by thr |
| Gln replaced by asn or lys | Thr replaced by ser |
| Glu replaced by asp | Trp replaced by tyr |
| Gly replaced by pro | Tyr replaced by trp or phe |
| His replaced by asn or gln | Val replaced by ile or leu |
| Ile replaced by leu or val | Nal replaced by Trp or Phe |

Substantial changes in function are made by selecting substitutions that are less conservative than those in Table 2, i.e., selecting residues that differ more significantly in their effect on maintaining (a) the structure of the peptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, argininyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the peptides provided herein.

In some embodiments, disclosed are polypeptides having at least about 60%, 70%, 80%, or 90% sequence identity to SEQ ID NO:1, SEQ ID NO:36, SEQ ID NO:56, SEQ ID NO:57, ro SEQ ID NO:58, SEQ ID NO: 65. For example, the disclosed polypeptides can have one, two, three, four, five, six, seven, or eight amino acid substitutions (conservative substitutions or non-conservative substitutions), or deletions or insertions of from 1 to 3 amino acid residues. As disclosed herein, the amino acid sequence of the disclosed polypeptides can have at least 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% homology with SEQ ID NO:1, (e.g., the sequence may contain additions, deletions, and/or substitutions). In some embodiments, the polypeptide sequence can comprise the amino acid sequences SEQ ID NO:2; SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22; SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32;

SEQ ID NO:33; SEQ ID NO:34; SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; SEQ ID NO:50; SEQ ID NO:51; SEQ ID NO:52; SEQ ID NO:53; SEQ ID NO:54; SEQ ID NO:55; SEQ ID NO:56; SEQ ID NO:57; SEQ ID NO:58; or a conservative variant thereof having at least about 60%, 70%, 80%, or 90% sequence identity (i.e., one, two, three, four, five, six, seven, or eight amino acid substitutions).

As disclosed herein, the amino acid sequence of the disclosed polypeptides can have at least 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% homology with SEQ ID NO:1, (e.g., the sequence may contain additions, deletions, and/or substitutions). In some embodiments, the polypeptide sequence can comprise the amino acid sequences SEQ ID NO:59; SEQ ID NO:60; SEQ ID NO:61; SEQ ID NO:62; SEQ ID NO:63; SEQ ID NO:64; SEQ ID NO:65; SEQ ID NO:66; SEQ ID NO:67; SEQ ID NO:68; SEQ ID NO:69; SEQ ID NO:70; SEQ ID NO:71; SEQ ID NO:72; SEQ ID NO:73; SEQ ID NO:74; SEQ ID NO:75; SEQ ID NO:76; SEQ ID NO:77; or a conservative variant thereof having at least about 60%, 70%, 80%, or 90% sequence identity (i.e., one, two, three, four, five, six, seven, or eight amino acid substitutions).

In certain embodiments, the disclosed polypeptides can comprise an amino acid sequence having amino acid substitutions that correspond to residues 18-23 of any of the polypeptides disclosed herein (e.g., SEQ ID NO:1; SEQ ID NO:36; SEQ ID NO:58, or SEQ ID NO: 65) or at least 1, 2, 3, 4, or 5 of these residues. For example, in some embodiments, the disclosed polypeptide can comprise the amino acid sequence SEQ ID NO:25; SEQ ID NO:26; SEQ ID NO:27; SEQ ID NO:28; SEQ ID NO:29; SEQ ID NO:30; SEQ ID NO:31; SEQ ID NO:32; SEQ ID NO:33; SEQ ID NO:48; SEQ ID NO:49; SEQ ID NO:50; SEQ ID NO:51; SEQ ID NO:52; or a conservative variant thereof having at least about 60%, 70%, 80%, or 90% sequence identity (i.e., one, two, three, four, five, six, seven, or eight amino acid substitutions).

In certain embodiments, the disclosed polypeptides can comprise an amino acid sequence having amino acid substitutions that correspond to residues 1-5 of any of the polypeptides disclosed herein (e.g., SEQ ID NO:1; SEQ ID NO:36; SEQ ID NO:56; SEQ ID NO:57; SEQ ID NO:58, or SEQ ID NO: 65) or at least 1, 2, 3, or 4 of these residues. For example, in some embodiments, the disclosed polypeptides can comprise the amino acid sequence SEQ ID NO:34; SEQ ID NO:35; SEQ ID NO:36; SEQ ID NO:38; SEQ ID NO:42; SEQ ID NO:44; SEQ ID NO:45; SEQ ID NO:46; SEQ ID NO:53; SEQ ID NO:54; SEQ ID NO:55; or a conservative variant thereof having at least about 60%, 70%, 80%, or 90% sequence identity (i.e., one, two, three, four, five, six, seven, or eight amino acid substitutions).

In specific embodiments, the disclosed polypeptides can comprise an amino acid sequence having an amino acid substitution at residue 1 of any of the polypeptides disclosed herein (e.g., SEQ ID NO:1, SEQ ID NO:36, SEQ ID NO:56, SEQ ID NO:57, SEQ ID NO:58,). For example, when the sequence of the polypeptide diverges from the above sequences, proline can be used to replace serine at residue 1. In some embodiments, the disclosed polypeptide can comprise the amino acid sequence SEQ ID NO:1, SEQ ID NO:36, SEQ ID NO:56, SEQ ID NO:57, SEQ ID NO:58; or a conservative variant thereof having at least about 60%, 70%, 80%, or 90% sequence identity (i.e., one, two, three, four, five, six, seven, or eight amino acid substitutions).

In certain embodiments, the disclosed polypeptides can comprise an amino acid sequence having amino acid substitutions that correspond to residues 6-17 of any of the polypeptides disclosed herein (e.g., SEQ ID NO:1; SEQ ID NO:36; SEQ ID NO:56; SEQ ID NO:57; or SEQ ID NO:58) or at least 1, 2, 3, 4, 5, 6, 7, 8, 9, 10, 11, or 12 of these residues. For example, in some embodiments, the disclosed polypeptide can comprise the amino acid sequence SEQ ID NO:35; SEQ ID NO:37; SEQ ID NO:39; SEQ ID NO:41; SEQ ID NO:43; SEQ ID NO:46; SEQ ID NO:47; or a conservative variant thereof having at least about 60%, 70%, 80%, or 90% sequence identity (i.e., one, two, three, four, five, six, seven, or eight amino acid substitutions).

In certain embodiments, when the sequence of the polypeptide diverges from the above sequences, the polypeptide can include deletions of a multiple amino acid region. The deletions can be external such as at the amino and/or carboxy terminus by 1, 2, 3, 4, 5, 6, 7, 8, 9, or 10 amino acids, particularly by 1, 2, 3, 4, or 5 amino acids, particularly by 1, 2, or 3 amino acids. The deletions can be internal such as at residues 2-22 of SEQ ID NO:1 by 1, 2, 3, 4, 5, or 6 amino acids, particularly by 1, 2, 3, 4, or 5 amino acids.

In specific embodiments, the polypeptide can comprise an amino acid sequence having amino acid deletions that correspond to residues 18-23 of any of the polypeptides disclosed herein (e.g., SEQ ID NO:1 or SEQ ID NO:36) or at least 1, 2, 3, 4, or 5 of these residues. For example, in some embodiments, the disclosed polypeptide can comprise the amino acid sequence SEQ ID NO:56; SEQ ID NO:57; or a conservative variant thereof having at least about 60%, 70%, 80%, or 90% sequence identity (i.e., one, two, three, four, five, six, seven, or eight amino acid substitutions). In some embodiments, the polypeptide can comprise at least residues 2 to 17 of SEQ ID NO:1 or a conservative variant thereof having at least about 60%, 70%, 80%, or 90% sequence identity (i.e., one, two, three, four, five, six, seven, or eight amino acid substitutions). In some embodiments, the polypeptide comprises at least residues 1 to 17 of SEQ ID NO:36 or a conservative variant thereof having at least about 60%, 70%, 80%, or 90% sequence identity (i.e., one, two, three, four, five, six, seven, or eight amino acid substitutions).

In certain embodiments, when the sequence of the polypeptide diverges from the above sequences, the polypeptide may extend beyond the above sequences at the amino and/or carboxy terminus by 1, 2, 3, 4, 5, 6, 7, 8, 9, or 10 amino acids, particularly by 1, 2, 3, 4, or 5 amino acids, particularly by 1, 2, or 3 amino acids.

As disclosed herein, the polypeptides can contain substitutions for the amino acids of the provided sequence. These substitutions can be similar to the amino acid (i.e., a conservative change) present in the disclosed sequences (e.g., an acidic amino acid in place of another acidic amino acid, a basic amino acid in place of a basic amino acid, a large hydrophobic amino acid in place of a large hydrophobic, etc.). The substitutions can also comprise amino acid analogs and mimetics. In a particular embodiment, the substitutions are predicted to promote helicity or helix formation.

The polypeptides can have capping, protecting and/or stabilizing moieties at the C-terminus and/or N-terminus. Such moieties are well known in the art and include, without limitation, amidation and acetylation. The polypeptides can also be lipidated or glycosylated at any amino acid (i.e., a glycopeptide). In particular, these polypeptides may be PEGylated to improve druggability.

The disclosed polypeptides can also comprise at least one D-amino acid instead of the native L-amino acid. In some embodiments, the disclosed polypeptides can comprise only D-amino acids. In a particular embodiment, the disclosed polypeptides comprise D-amino acids which are spaced apart by about 1, 2, 3, and/or 4 (e.g., 3) consecutive L-amino acids.

The polypeptides can contain at least one derivative of standard amino acids, such as, without limitation, fluorinated residues or nonstandard amino acids (e.g., beta-amino acids). In yet another embodiment, the peptide may also be circulated head to tail or locally involving a few residues.

Recombinant Vectors and Expression Systems

In certain embodiments, the disclosure relates to recombinant vectors comprising a nucleic acid encoding peptide disclosed herein. In certain embodiments, the disclosure relates to expression systems comprising a recombinant vector comprising a nucleic acid encoding peptide disclosed herein. In certain embodiments, the disclosure relates to cells comprising a recombinant vector comprising a nucleic acid encoding peptide disclosed herein.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "vector" or "expression vector " refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Protein "expression systems" refer to in vivo and in vitro (cell free) systems. Systems for recombinant protein expression typically utilize cells transfecting with a DNA expression vector that contains the template. The cells are cultured under conditions such that they translate the desired protein. Expressed proteins are extracted for subsequent purification. In vivo protein expression systems using prokaryotic and eukaryotic cells are well known. Also, some proteins are recovered using denaturants and protein-refolding procedures. In vitro (cell-free) protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vectors, these extracts and components can synthesize proteins of interest. Cell-free systems typically do not contain proteases and enable labeling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

A "selectable marker" is a nucleic acid introduced into a recombinant vector that encodes a polypeptide that confers a trait suitable for artificial selection or identification (report gene), e.g., beta-lactamase confers antibiotic resistance, which allows an organism expressing beta-lactamase to survive in the presence antibiotic in a growth medium. Another example is thymidine kinase, which makes the host sensitive to ganciclovir selection. It may be a screenable marker that allows one to distinguish between wanted and unwanted cells based on the presence or absence of an expected color. For example, the lac-z-gene produces a beta-galactosidase enzyme which confers a blue color in the presence of X-gal (5-bromo-4-chloro-3-indolyl-β-D-galactoside). If recombinant insertion inactivates the lac-z-gene, then the resulting colonies are colorless. There may be one or more selectable markers, e.g., an enzyme that can complement to the inability of an expression organism to synthesize a particular compound required for its growth (auxotrophic) and one able to convert a compound to another that is toxic for growth. URA3, an orotidine-5' phosphate decarboxylase, is necessary for uracil biosynthesis and can complement ura3 mutants that are auxotrophic for uracil. URA3 also converts 5-fluoroorotic acid into the toxic compound 5-fluorouracil.

Additional contemplated selectable markers include any genes that impart antibacterial resistance or express a fluorescent protein. Examples include, but are not limited to, the following genes: amp$^r$, cam$^r$, tet$^r$, blasticidin$^r$, neo$^r$, hyg$^r$, abx$^r$, neomycin phosphotrans ferase type II gene (nptII), p-glucuronidase (gus), green fluorescent protein (gfp), egfp, yfp, mCherry, p-galactosidase (lacZ), lacZa, lacZAM15, chloramphenicol acetyltransferase (cat), alkaline phosphatase (phoA), bacterial luciferase (luxAB), bialaphos resistance gene (bar), phosphomannose isomerase (pmi), xylose isomerase (xylA), arabitol dehydrogenase (at1D), UDP-glucose:galactose-1-phosphate uridyltransferasel (galT), feedback-insensitive a subunit of anthranilate synthase (OASA1D), 2-deoxyglucose (2-DOGR), benzyladenine-N-3-glucuronide, E. coli threonine deaminase, glutamate 1-semialdehyde aminotransferase (GSA-AT), D-amino acidoxidase (DAAO), salt-tolerance gene (rstB), ferredoxin-like protein (pflp), trehalose-6-P synthase gene (AtTPS1), lysine racemase (lyr), dihydrodipicolinate synthase (dapA), tryptophan synthase beta 1 (AtTSB 1), dehalogenase (dhlA), mannose-6-phosphate reductase gene (M6PR), hygromycin phosphotransferase (HPT), and D-serine ammonialyase (dsdA).

A "label" refers to a detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "label receptor" refers to incorporation of a heterologous polypeptide in the receptor. A label includes the incorporation of a radiolabeled amino acid or the covalent attachment of biotinyl moieties to a polypeptide that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}$S or $^{131}$I) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

In certain embodiments, the disclosure relates to recombinant polypeptides comprising sequences disclosed herein or variants or fusions thereof wherein the amino terminal end or the carbon terminal end of the amino acid sequence are optionally attached to a heterologous amino acid sequence, label, or reporter molecule.

In certain embodiments, the disclosure relates to the recombinant vectors comprising a nucleic acid encoding a polypeptide disclosed herein or chimeric protein thereof. In certain embodiments, the recombinant vector optionally comprises a mammalian, human, insect, viral, bacterial, bacterial plasmid, yeast associated origin of replication or gene such as a gene or retroviral gene or lentiviral LTR, TAR, RRE, PE, SLIP, CRS, and INS nucleotide segment or gene selected from tat, rev, nef, vif, vpr, vpu, and vpx or structural genes selected from gag, pol, and env.

In certain embodiments, the recombinant vector optionally comprises a gene vector element (nucleic acid) such as a selectable marker region, lac operon, a CMV promoter, a hybrid chicken B-actin/CMV enhancer (CAG) promoter, tac promoter, T7 RNA polymerase promoter, SP6 RNA polymerase promoter, SV40 promoter, internal ribosome entry site (IRES) sequence, cis-acting woodchuck post regulatory regulatory element (WPRE), scaffold-attachment region (SAR), inverted terminal repeats (ITR), FLAG tag coding region, c-myc tag coding region, metal affinity tag coding region, streptavidin binding peptide tag coding region, polyHis tag coding region, HA tag coding region, MBP tag coding region, GST tag coding region, polyadenylation coding region, SV40 polyadenylation signal, SV40 origin of replication, Col E1 origin of replication, f1 origin, pBR322 origin, or pUC origin, TEV protease recognition site, loxP site, Cre recombinase coding region, or a multiple cloning site such as having 5, 6, or 7 or more restriction sites within a continuous segment of less than 50 or 60 nucleotides or having 3 or 4 or more restriction sites with a continuous segment of less than 20 or 30 nucleotides.

Vaccine Compositions

Also disclosed are vaccine compositions containing any of the disclosed polypeptides in a pharmaceutically acceptable vehicle, diluent or excipient. Although not required, the vaccine compositions optionally contain one or more immunostimulants. An immunostimulant refers to essentially any substance that enhances or potentiates an immune response (antibody or cell-mediated) to an exogenous antigen. One preferred type of immunostimulant is an adjuvant. The vaccine can optionally contain a pharmaceutically acceptable adjuvant.

Many adjuvants contain a substance designed to protect the polypeptide from rapid catabolism, such as aluminum hydroxide or mineral oil, and a stimulator of immune responses, such as lipid A, *Bortadella pertussis* or *Mycobacterium tuberculosis* derived proteins. The adjuvant may be a submicron oil-in-water emulsion of a metabolizable oil and an emulsifying agent. For example, the adjuvant may comprise MF59™, which is a sub-micron oil-in-water emulsion of a squalene, polyoxyethylene sorbitan monooleate (Tween™ 80) and sorbitan trioleate. The adjuvant may also be a combination of the TLR4 agonist MPL (3-O-desacyl-4'-monophosphoryl lipid A) and aluminum salt, e.g., ASO4 (GlaxoSmithKline, Philadelphia, Pa.).

Certain adjuvants are commercially available as, for example, Freund's Incomplete Adjuvant and Complete Adjuvant (Difco Laboratories, Detroit, Mich.); Merck Adjuvant 65 (Merck and Company, Rahway, N.J.); AS01, AS02, AS03, and ASO4 (GlaxoSmithKline, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, may also be used as adjuvants.

The adjuvant composition can be a composition that induces an anti-inflammatory immune response (antibody or cell-mediated). Accordingly, high levels of anti-inflammatory cytokines (anti-inflammatory cytokines may include, but are not limited to, interleukin 4 (IL-4), interleukin 5 (IL-5), interleukin 10 (IL-10), and transforming growth factor beta (TGFβ). Optionally, an anti-inflammatory response would be mediated by CD4+ T helper cells. Bacterial flagellin has been shown to have adjuvant activity (McSorley et al., J. Immunol. 169:3914-19, 2002). Also disclosed are polypeptide sequences that encode flagellin proteins that can be used in adjuvant compositions. Optionally, the adjuvants increase lipopolysaccharide (LPS) responsiveness. Illustrative adjuvants include but are not limited to, monophosphoryl lipid A (MPL), aminoalkyl glucosaminide 4-phosphates (AGPs), including, but not limited to RC-512, RC-522, RC-527, RC-529, RC-544, and RC-560 (Corixa, Hamilton, Mont.).

In addition, the adjuvant composition can be one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a subject will support an immune response that includes Th1- and Th2-type responses. Optionally, the level of Th1-type cytokines will increase to a greater extent than the level of Th2-type cytokines. The levels of these cytokines may be readily assessed using standard assays. Certain adjuvants for eliciting a predominantly Th1-type response include, for example, a combination of monophosphoryl lipid A, preferably 3-de-O-acylated monophosphoryl lipid A, together with an aluminum salt adjuvants are available from Corixa Corporation (Seattle, Wash.). CpG-containing oligonucleotides (in which the CpG dinucleotide is unmethylated) also induce a predominantly Th1 response. Another adjuvant comprises a saponin, such as Quil A, or derivatives thereof, including QS21 and QS7 (Aquila Biopharmaceuticals Inc., Framingham, Mass.); Escin; Digitonin; or Gypsophila or Chenopodium quinoa saponins.

Additional illustrative adjuvants for use in the disclosed vaccine compositions include Montamide ISA 720 (Seppic, France), SAF (Chiron, Calif., United States), ISCOMS (CSL), MF-59 (Chiron), the SBAS series of adjuvants (e.g., SBAS-2 or SBAS-4, available from GlaxoSmithKline, Philadelphia, Pa.), Detox (Enhanzyn™) (Corixa, Hamilton, Mont.), RC-529 (Corixa, Hamilton, Mont.) and other aminoalkyl glucosaminide 4-phosphates (AGPs).

Pharmaceutical Compositions

The disclosed polypeptides can be used therapeutically in combination with a pharmaceutically acceptable carrier. The carrier would naturally be selected to minimize any degradation of the active ingredient and to minimize any adverse side effects in the subject, as would be well known to one of skill in the art.

The disclosed polypeptides may be in solution, suspension, incorporated into microparticles, liposomes, or cells, or formed into tablets, gels, or suppositories. Suitable carriers and their formulations are described in Remington: The Science and Practice of Pharmacy (22nd ed.) eds. Loyd V. Allen, Jr., et al., Pharmaceutical Press, 2012. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of vaccines to humans, including solutions such as sterile water, saline, and buffered solutions at physiological pH. Pharmaceutical compositions may include carriers, thickeners, diluents, buffers, preservatives, surface active agents and the like in addition to the vaccine. Pharmaceutical compositions may also include one or more active ingredients such as antimicrobial agents, anti-inflammatory agents, anesthetics, and the like. The disclosed polypeptides are preferably formulated for delivery via intranasal, intramuscular, subcutaneous, transdermal or sublingual administration.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

For an oral administration form, the disclosed polypeptides can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, cornstarch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the disclosed polypeptides may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the disclosure or their physiologically tolerable salts in a pharmaceutically acceptable solvent, such as ethanol or water, or a mixture of such solvents. If required, the formulation may additionally contain other pharmaceutical auxiliaries such as surfactants, emulsifiers and stabilizers as well as a propellant.

For subcutaneous or intravenous administration, the disclosed polypeptides, if desired with the substances customary therefore such as solubilizers, emulsifiers or further auxiliaries are brought into solution, suspension, or emulsion. The disclosed polypeptides may also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, the formulations may be prepared by mixing the polypeptide with a suitable non-irritating excipient, such as cocoa butter, synthetic glyceride esters or polyethylene glycols, which are solid at ordinary temperatures, but liquefy and/or dissolve in the rectal cavity to release the drug.

Parenteral administration of the disclosed polypeptides, if used, is generally characterized by injection. Injectables can be prepared in conventional forms, either as liquid solutions or suspensions, solid forms suitable for solution of suspension in liquid prior to injection, or as emulsions.

In certain embodiments, it is contemplated that compositions comprising the disclosed polypeptides can be extended release formulations. Typical extended release formations utilize an enteric coating. Typically, a barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaluronic acid, chitin, chitosan and the like; other natural polymers, such as proteins (albumin, gelatin etc.), poly-L-lysine; sodium poly (acrylic acid); poly(hydroxyalkylmethacrylates) (for example poly(hydroxyethylmethacrylate)); carboxypolymethylene (for example Carbopol™); carbomer; polyvinylpyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethylcellulose (HMC), hydroxyethylcellulose (HEC), hydroxypropylcellulose (HPC), methylcellulose (MC), ethylcellulose (EC), carboxyethylcellulose (CEC), ethylhydroxyethylcellulose (EHEC), carboxymethylhydroxyethylcellulose (CMHEC), hydroxypropylmethyl-cellulose (HPMC), hydroxypropylethylcellulose (HPEC) and sodium carboxymethylcellulose (Na-CMC); as well as copolymers and/or (simple) mixtures of any of the above polymers. Certain of the above-mentioned polymers may further be crosslinked by way of standard techniques.

The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxyl groups and hydroxypropoxyl groups will give rise to changes in the rate of release of drug from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Microspheres of polylactide, polyglycolide, and their copolymers poly(lactide-co-glycolide) may be used to form sustained-release protein delivery systems. The disclosed polypeptides can be entrapped in the poly(lactide-co-glycolide) microsphere depot by a number of methods, including formation of a water-in-oil emulsion with water-borne protein and organic solvent-borne polymer (emulsion method), formation of a solid-in-oil suspension with solid protein dispersed in a solvent-based polymer solution (suspension method), or by dissolving the protein in a solvent-based polymer solution (dissolution method). One can attach poly(ethylene glycol) to proteins (PEGylation) to increase the in vivo half-life of circulating therapeutic proteins and decrease the chance of an immune response.

Liposomal suspensions (including liposomes targeted to viral antigens) may also be prepared by conventional methods to produce pharmaceutically acceptable carriers. This may be appropriate for the delivery of free nucleosides, acyl nucleosides or phosphate ester prodrug forms of the nucleoside compounds according to the present disclosure.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter indications. Dosage can vary, and can be administered in one or more dose administrations daily, for one or several days. Guidance can be found in the literature for appropriate dosages for given classes of pharmaceutical products. A typical dosage of the disclosed vaccine used alone might range from about 1 mg/kg to up to 100 mg/kg of body weight or more per vaccination, such as 10 µg/kg to 50 mg/kg, or 50 µg/kg to 10 mg/kg, depending on the factors mentioned above.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Some of the disclosed polypeptides may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g., about 10, 25, 50, 100, 200, 300 or 400 mg per unit dosage.

The disclosed polypeptides can also be used to supplement existing human vaccines to improve cross protection. Therefore, the disclosed compositions can further include (or be administered in combination with) a whole inactivated virus, split viral vaccine, live attenuated dengue virus vaccine, live attenuated ZIKV virus vaccine, or another virus-like particle (VLP) vaccine, as well as DNA vaccines.

The disclosed compositions can further include (or be administered in combination with) one or more of classes of antivirals, antibiotics, steroids, analgesics, anti-inflammatory agents, anti-histaminic agents, or any combination thereof.

In a specific embodiment, the disclosed polypeptides can be administered with (in combination in the same composition, in combination but in separate compositions, or sequentially) an antiviral. Examples of suitable antivirals can be used in such combinations include but are not limited to, Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; Zinviroxime.

Methods of administering peptides include, but are not limited to, parenteral administration (e.g., intradermal, intramuscular, intraperitoneal, intravenous and subcutaneous), epidural, and mucosal (e.g., intranasal and oral routes). In a specific embodiment, the peptides or chimeric proteins are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents.

Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,20; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903. In a specific embodiment, it may be desirable to administer the pharmaceutical compositions locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers.

In certain embodiments, the aerosolizing agent or propellant is a hydrofluoroalkane, 1,1,1,2-tetrafluoroethane, 1,1,1, 2,3,3,3 -heptafluoropropane, propane, n-butane, isobutene, carbon dioxide, air, nitrogen, nitrous oxide, dimethyl ether, trans-1,3,3,3-tetrafluoroprop-1-ene, or combinations thereof.

The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems. For peptides and fusion proteins, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. Further, the dosage and frequency of administration of proteins may be reduced by enhancing uptake and tissue penetration of the fusion proteins by modifications such as, for example, lipidation.

The compositions include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. In certain embodiments, the pharmaceutical compositions contain a pharmaceutically acceptable excipient that is a solubilizing agent such as a lipid, cholesterol, fatty acid, fatty acid alkyl ester, linoleic acid, oleic acid arachidonic acid, saccharide, polysaccharide, cyclodextrin, 2-hydoxypropyl(cyclodextrin), or combinations thereof.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

One embodiment provides a pharmaceutical pack or kit comprising one or more containers filled with peptides disclosed herein. Additionally, one or more other prophylactic or therapeutic agents useful for the treatment of a disease can also be included in the pharmaceutical pack or kit. One embodiment provides a pharmaceutical pack or kit including one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration.

In certain embodiment, this disclosure contemplates pharmaceutical compositions comprising proteins disclosed herein and pharmaceutically acceptable excipient. In certain embodiments, this disclosure contemplates the production of a medicament comprising proteins disclosed herein and uses for methods disclosed herein.

In certain embodiments, the disclosure relates to pharmaceutical compositions comprising proteins disclosed herein and a pharmaceutically acceptable excipient. In certain embodiments, the composition is a pill or in a capsule or the composition is an aqueous buffer, e.g., a pH between 6 and 8. In certain embodiments, the pharmaceutically acceptable excipient is selected from a filler, glidant, binder, disintegrant, lubricant, and saccharide.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents solvents or vehicles include water, ethanol, polyols (propylene glycol, polyethylene glycol, glycerol, and the like), suitable mixtures thereof, vegetable (such as olive oil, sesame oil and viscoleo) and injectable organic esters such as ethyl oleate. Prevention of the action of microorganisms may be controlled by addition of any of various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the proteins may be admixed with at least one inert customary excipient (or carrier) such as sodium citrate or dicalcium phosphate or: (a) fillers or extenders, as for example, starches, lactose, sucrose, glucose, mannitol and silicic acid, (b) binders, as for example, carboxymethylcellulose, alginates, gelatin, polyvinylpyrrolidone, sucrose, and acacia, (c) humectants, as for example, glycerol (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Liquid dosage forms for oral administration include pharmaceutically acceptable emulsions, solutions, suspensions, syrups, and elixirs. In addition to the proteins, the liquid dosage forms may contain inert diluents commonly used in the art, such as water or other solvents, solubilizing agents and emulsifiers, for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

In certain embodiments, production processes are contemplated which two components, proteins disclosed herein and a pharmaceutical carrier, are provided already in a combined dry form ready to be reconstituted together. In other embodiments, it is contemplated that proteins disclosed herein and a pharmaceutical carrier are admixed to provide a pharmaceutical composition.

Providing a pharmaceutic composition is possible in a one-step process, simply by adding a suitable pharmaceutically acceptable diluent to the composition in a container. In certain embodiments, the container is preferably a syringe for administering the reconstituted pharmaceutical composition after contact with the diluent. In certain embodiments, the coated proteins can be filled into a syringe, and the syringe can then be closed with the stopper. A diluent is used in an amount to achieve the desired end-concentration. The pharmaceutical composition may contain other useful component, such as ions, buffers, excipients, stabilizers, etc.

A "dry" pharmaceutical composition typically has only a residual content of moisture, which may approximately correspond to the moisture content of comparable commercial products, for example, has about 12% moisture as a dry product. Usually, the dry pharmaceutical composition according to the present invention has a residual moisture content preferably below 10% moisture, more preferred below 5% moisture, especially below 1% moisture. The pharmaceutical composition can also have lower moisture content, e.g. 0.1% or even below. In certain embodiments, the pharmaceutical composition is provided in dry in order to prevent degradation and enable storage stability.

A container can be any container suitable for housing (and storing) pharmaceutically compositions such as syringes, vials, tubes, etc. The pharmaceutical composition may then preferably be applied via specific needles of the syringe or via suitable catheters. A typical diluent comprises water for injection, and NaCl (preferably 50 to 150 mM, especially 110 mM), $CaC_{12}$ (preferably 10 to 80 mM, especially 40 mM), sodium acetate (preferably 0 to 50 mM, especially 20 mM) and mannitol (preferably up to 10% w/w, especially 2% w/w). Preferably, the diluent can also include a buffer or buffer system so as to buffer the pH of the reconstituted dry composition, preferably at a pH of 6.2 to 7.5, especially at pH of 6.9 to 7.1.

In certain embodiments, the diluent is provided in a separate container. This can preferably be a syringe. The diluent in the syringe can then easily be applied to the container for reconstitution of the dry compositions. If the container is also a syringe, both syringes can be finished together in a pack. It is therefore preferred to provide the dry compositions in a syringe, which is finished with a diluent syringe with a pharmaceutically acceptable diluent for reconstituting, said dry and stable composition.

In certain embodiments, this disclosure contemplates a kit comprising a pharmaceutical composition disclosed herein and a container with a suitable diluent. Further components of the kit may be instructions for use, administration means, such as syringes, catheters, brushes, etc. (if the compositions are not already provided in the administration means) or other components necessary for use in medical (surgical) practice, such as substitute needles or catheters, extra vials or further wound cover means. In certain embodiments, the kit comprises a syringe housing the dry and stable hemostatic composition and a syringe containing the diluent (or provided to take up the diluent from another diluent container).

Method of Making

The polypeptides disclosed herein can be prepared in a variety of ways, according to known methods. In some embodiments, the polypeptides can be purified from appropriate sources (e.g., bacterial or animal cultured cells or tissues, optionally transformed) by immunoaffinity purification. For example, SEQ ID NO:1 can be derived from frogs including *Hydrophylax bahuvistara* and *Hylarana aurantiaca*, found in the Western Ghats of southwestern India. The availability of nucleic acid molecules encoding the polypeptides enables production of the protein using in vitro expression methods and cell-free expression systems known in the art. In vitro transcription and translation systems are commercially available, e.g., from Promega™ Biotech (Madison, Wis.) or Gibco®-BRL (Gaithersburg, Md.).

Larger quantities of the polypeptides can be produced by expression in a suitable prokaryotic or eukaryotic system. For example, part or all of a DNA molecule encoding for a polypeptides can be inserted into a plasmid vector adapted for expression in a bacterial cell, such as *E. coli*. Such vectors comprise the regulatory elements necessary for expression of the DNA in the host cell positioned in such a manner as to permit expression of the DNA in the host cell.

Such regulatory elements required for expression include promoter sequences, transcription initiation sequences and, optionally, enhancer sequences.

Polypeptides produced by gene expression in a recombinant prokaryotic or eukaryotic system may be purified according to methods known in the art. A commercially available expression/secretion system can be used, whereby the recombinant protein is expressed and thereafter secreted from the host cell, and readily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope or the hemaglutinin epitope. Such methods are commonly used by skilled practitioners.

The polypeptides can also be chemically synthesized. For example, the peptides may be synthesized using a solid-phase method. Steward, J. M. and Young, J. D., Solid Phase Peptide Synthesis, 2nd Ed., Pierce Chemical Company, Rockford, Ill., (1984) using an Applied Biosystem synthesizer.

Similarly, multiple fragments may be synthesized then linked together to form larger fragments. These synthetic peptide fragments can also be made with amino acid substitutions at specific locations to test for antiviral activity in vitro and in vivo. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, Vol. 1, Academic Press (New York). In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid is then either attached to an inert solid support or utilized in solution by adding the next amino acid in the sequence having the complimentary (amino or carboxyl) group suitably protected and under conditions suitable for forming the amide linkage. The protecting group is then removed from this newly added amino acid residue and the next amino acid (suitably protected) is added, and so forth. After all the desired amino acids have been linked in the proper sequence, any remaining protecting groups (and any solid support) are removed sequentially or concurrently to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

One suitable method of preparing polypeptides involves solid phase peptide synthesis wherein the amino acid α-N-terminal is protected by an acid or base sensitive group. Such protecting groups should have the properties of being stable to the conditions of peptide linkage formation while being readily removable without destruction of the growing peptide chain or racemization of any of the chiral centers contained therein. Suitable protecting groups are 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobornyloxycarbonyl, α,α-dimethyl-3, 5-dimethoxybenzyloxycarbonyl, o-nitrophenylsulfenyl, 2-cyano-t-butyloxycarbonyl, and the like. Other side chain protecting groups are, for side chain amino groups like lysine and arginine, 2,2,5,7,8-pentamethylchroman-6-sulfonyl (pmc), nitro, p-toluenesulfonyl, 4-methoxybenzenesulfonyl, Cbz, Boc, and adamantyloxycarbonyl; for tyrosine, benzyl, o-bromobenzyloxy-carbonyl, 2,6-dichlorobenzyl, isopropyl, t-butyl (t-Bu), cyclohexyl, cyclopenyl and acetyl (Ac); for serine, t-butyl, benzyl and tetrahydropyranyl; for histidine, trityl, benzyl, Cbz, p-toluenesulfonyl and 2,4-dinitrophenyl; for tryptophan, formyl; for asparticacid and glutamic acid, benzyl and t-butyl and for cysteine, triphenylmethyl (trityl).

In the solid phase peptide synthesis method, the α-C-terminal amino acid is attached to a suitable solid support or resin. Suitable solid supports useful for the above synthesis are those materials which are inert to the reagents and reaction conditions of the stepwise condensation-deprotection reactions, as well as being insoluble in the media used. A solid support for synthesis of α-C-terminal carboxy peptides is 4-hydroxymethylphenoxymethyl-copoly(styrene-1% divinylbenzene). A solid support for α-C-terminal amide peptides is the 4-(2',4'-dimethoxyphenyl-Fmoc-aminomethyl)phenoxyacetamidoethyl resin available from Applied Biosystems (Foster City, Calif.). The α-C-terminal amino acid is coupled to the resin by means of N,N'-dicyclohexylcarbodiimide (DCC), N,N'-diisopropylcarbodiimide (DIC) or O-benzotriazol-1-yl-N,N,N',N'-tetramethyluroniumhexafluorophosphate (HBTU), with or without 4-dimethylaminopyridine (DMAP), 1-hydroxybenzotriazole (HOBT), benzotriazol-1-yloxy-tris(dimethylamino)phosphoniumhexafluorophosphate (BOP) or bis(2-oxo-3-oxazolidinyl)phosphine chloride (BOPCl), mediated coupling for from about 1 to about 24 hours at a temperature of between 10° C. and 50° C. in a solvent such as dichloromethane or DMF. When the solid support is 4-(2',4'-dimethoxyphenyl-Fmoc-aminomethyl)phenoxy-acetamidoethyl resin, the Fmoc group is cleaved with a secondary amine, preferably piperidine, prior to coupling with the α-C-terminal amino acid as described above.

A method for coupling to the deprotected 4 (2',4'-dimethoxyphenyl-Fmoc-aminomethyl)phenoxy-acetamidoethyl resin is O-benzotriazol- 1-yl-N,N,N',N'-tetramethyluroniumhexafluorophosphate (HBTU, 1 equiv.) and 1-hydroxybenzotriazole (HOBT, 1 equiv.) in DMF. The coupling of successive protected amino acids can be carried out in an automatic polypeptide synthesizer as is well known in the art.

In one embodiment, the α-N-terminus in the amino acids of the growing peptide chain are protected with Fmoc. The removal of the Fmoc protecting group from the α-N-terminal side of the growing peptide is accomplished by treatment with a secondary amine, preferably piperidine. Each protected amino acid is then introduced in about 3-fold molar excess, and the coupling is preferably carried out in DMF. The coupling agent is normally O-benzotriazol-1-yl-N,N,N', N'-tetramethyluroniumhexafluorophosphate (HBTU, 1 equiv.) and 1-hydroxybenzotriazole (HOBT, 1 equiv.). At the end of the solid phase synthesis, the polypeptide is removed from the resin and deprotected, either in successively or in a single operation.

Removal of the polypeptide and deprotection can be accomplished in a single operation by treating the resin-bound polypeptide with a cleavage reagent comprising thianisole, water, ethanedithiol and trifluoroacetic acid. In cases wherein the α-C-terminal of the polypeptide is an alkylamide, the resin is cleaved by aminolysis with an alkylamine. Alternatively, the peptide may be removed by transesterification, e.g. with methanol, followed by aminolysis or by direct transamidation. The protected peptide may be purified at this point or taken to the next step directly. The removal of the side chain protecting groups is accomplished using the cleavage cocktail described above. The fully deprotected peptide can be purified by a sequence of chromatographic steps employing any or all of the following types: ion exchange on a weakly basic resin (acetate form); hydrophobic adsorption chromatography on underivitized polystyrene-divinylbenzene (for example, Amberlite XAD); silica gel adsorption chromatography; ion exchange chromatography on carboxymethylcellulose; partition chromatography, e.g. on Sephadex G-25, LH-20 or countercurrent distribution; high performance liquid chromatography (HPLC), especially reverse-phase HPLC on octyl- or octadecylsilyl-silica bonded phase column packing.

Polypeptides, prepared by the aforementioned methods, may be analyzed and verified according to standard procedures. For example, such polypeptides may be subjected to amino acid sequence analysis, according to known methods.

The activity of the polypeptides can be measured by any method, such as measuring the ability of the polypeptide to block infection of cells by for example, dengue or the Zika virus.

Methods of Using

The present disclosure also encompasses methods of using the polypeptides disclosed herein. The polypeptides and compositions provided herein can be used to treat viral infectious diseases. Viruses are infectious agents that can typically replicate inside the living cells of organisms. Virus particles (virions) usually consist of nucleic acids, a protein coat, and in some cases an envelope of lipids that surrounds the protein coat. The shapes of viruses range from simple helical and icosahedral forms to more complex structures. Virally coded protein subunits will self-assemble to form a capsid, generally requiring the presence of the virus genome. Complex viruses can code for proteins that assist in the construction of their capsid. Proteins associated with nucleic acid are known as nucleoproteins, and the association of viral capsid proteins with viral nucleic acid is called a nucleocapsid.

In some embodiments, the disclosure relates to methods of treating a subject infected with an envelope RNA virus. Examples of envelope RNA viruses include human immunodeficiency virus (HIV), influenza, hepatitis, Zika virus, and dengue.

In certain embodiments, the disclosure relates to methods of treating a subject diagnosed with Zika virus (ZIKV) infection. In certain embodiments, the disclosure relates to methods of preventing ZIKV infection in a subject. Zika virus (ZIKV) is an emerging arthropod-borne human pathogen in the family Flaviviridae (genus *flavivirus*) first isolated in 1947 from a febrile sentinel rhesus monkey in the Zika forest of Uganda. Though mainly transmitted by the *Aedes aegypti* mosquito, current reports strongly suggest that the virus is being transmitted perinatally, sexually and via blood transfusion. ZIKV infections are usually self-limiting with 80% of infected individuals clinically asymptomatic. Symptoms for patients that become ill are usually mild and non-life threating. Symptoms include fever, maculopapular rash, joint pain and/or conjunctivitis, muscle pain, headache and retro-orbital pain. Recently, a higher than normal incidence of Gullain-Barre Syndrome (GBS), the most frequent cause of non-poliovirus associated acute flaccid paralysis, and primary microcephaly cases have been linked to ZIKV outbreaks in French Polynesia and Brazil. GBS is a serious disease believed to be initiated by an immune-mediated response to antigenic exposure from certain viruses or bacterial infections. Roughly 20% of the patients are left with severe disability and approximately 5% of the patients die. Also of great concern is the apparent correlation of ZIKV infections with a 20-fold increase in the incidence of microcephaly cases reported in Brazil in 2015. Among the symptoms, the most common are seizures, mental retardation, development delay, cerebral palsy, hearing and vision loss.

The mechanism of infection of ZIKV has not been well studied, but the replication cycle of the virus may be similar to other flaviviruses such as DFV. Human skin inoculated with saliva from a ZIKV infected mosquito leads to infection of epidermal keratinocytes, skin fibroblasts, and Langerhans cells. ZIKV continues to spread throughout the human host by way of lymph nodes and bloodstream. ZIKV genome replication occurs at intracellular compartments in the endoplasmic reticulum by a membrane-bound viral replication complex consisting of viral non-structural proteins, viral RNA, and host proteins, the identity of which are mostly unknown. The genome of ZIKV is a single-stranded (+)-RNA molecule approximately 10.7 kb in length with two non-coding flanking regions (NCR) known as 5'-NCR and 3'-NCR. The ZIKV RNA genome contains a single open reading frame (ORF) encoding a 3,419 amino acid polypeptide, which is cleaved into three structural proteins (C, prM and E) and seven non-structural proteins (NS1, NS2a, NS2b, NS3, NS4a, NS4b and NS5). The complex first transcribes genomic plus-strand RNA into a complementary minus strand RNA intermediate resulting in the formation of a duplex RNA. The minus strand of this duplex serves as a template for multiple rounds of plus-strand RNA synthesis. Viral RNA synthesis occurs through an asymmetric replication cycle in which ten times more plus-strand than minus-strand RNA is synthesized.

In certain embodiments, the disclosure relates to methods of treating a subject diagnosed with dengue infection. In certain embodiments, the subject is diagnosed with dengue of stereotypes 1, 2, 3, or 4.

In certain embodiments, the disclosure relates to methods of treating a subject diagnosed with influenza infection. In certain embodiments, the subject is diagnosed with influenza A virus, influenza B virus, influenza C virus, avian influenza, or SARS, including subtype H1N1, H3N2, H7N9, H5N1, H7N7, H1N2, H9N2, H7N2, H7N3, H1ON$_7$, H5N1, H5N1, H5N1 Duck/MN/1525/81, H5N2, H7N1, H7N7 and H9N2).

In certain embodiments, the disclosure relates to methods of treating a subject diagnosed with HIV. HIV is a lentivirus (a member of the retrovirus family) that causes acquired immunodeficiency syndrome (AIDS). Lentiviruses are transmitted as single-stranded, positive-sense, enveloped RNA viruses. Upon entry of the target cell, the viral RNA genome is converted to double-stranded DNA by a virally encoded reverse transcriptase. This viral DNA is then integrated into the cellular DNA by a virally encoded integrase, along with host cellular co-factors. There are two species of HIV. HIV-1 is sometimes termed LAV or HTLV-III.

HIV is typically treated with a combination of antiviral agent, e.g., two nucleoside-analogue reverse transcription inhibitors and one non-nucleoside-analogue reverse transcription inhibitor or protease inhibitor. The three-drug combination is commonly known as a triple cocktail. In certain embodiments, the disclosure relates to treating a subject diagnosed with HIV by administering a pharmaceutical composition disclosed herein in combination with two nucleoside-analogue reverse transcription inhibitors and one non-nucleoside-analogue reverse transcription inhibitor or protease inhibitor. Examples of non-nucleoside-analogue reverse transcription inhibitor or protease inhibitors include emtricitabine, tenofovir, efavirenz, raltegravir, ritonavir, and darunavir.

In certain embodiments, the disclosure relates to methods of treating a subject diagnosed with hepatitis C (HCV) of hepatitis B (HBV). The hepatitis C virus is a single-stranded, positive sense RNA virus. It is the only known member of the hepacivirus genus in the family Flaviviridae. There are six major genotypes of the hepatitis C virus, which are indicated numerically. The hepatitis C virus particle consists of a core of genetic material (RNA), surrounded by an icosahedral protective shell, and further encased in a lipid envelope. Two viral envelope glycoproteins, E1 and E2, are embedded in the lipid envelope. The genome consists of a single open reading frame translated to produce a single protein. This large pre-protein is later cut by cellular and viral proteases into smaller proteins that allow viral replication within the host cell, or assemble into the mature viral particles, e.g., E1, E2, NS2, NS3, NS4, NS4A, NS4B, NS5, NSSA, and NS5B.

Hepatitis B virus is a hepadnavirus. The virus particle, (virion) consists of an outer lipid envelope and an icosahedral nucleocapsid core composed of protein. The genome of HBV is made of circular DNA, but the DNA is not fully double-stranded. One end of the strand is linked to the viral DNA polymerase. The virus replicates through an RNA intermediate form by reverse transcription. Replication typically takes place in the liver where it causes inflammation (hepatitis). The virus spreads to the blood where virus-specific proteins and their corresponding antibodies are found in infected people. Blood tests for these proteins and antibodies are used to diagnose the infection.

The methods disclosed herein can include administering the disclosed polypeptides to a subject with an envelope virus such as HIV, influenza, dengue, or ZIKV. The disclosed polypeptides can be administered in a number of ways. For example, the disclosed polypeptides can be administered intramuscularly, intranasally, or by microneedle in the skin. The compositions may be administered orally, intravenously, subcutaneously, transdermally (e.g., by microneedle), intraperitoneally, ophthalmically, vaginally, rectally, sublingually, or by inhalation.

The polypeptide will generally be administered in an "effective amount," by which is meant any amount of a polypeptide that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

In certain embodiments, pharmaceutical compositions disclosed herein are administered in combination with a second antiviral agent. In certain embodiments, the second antiviral agent is oseltamivir, zanamivir, and/or peramivir. In certain embodiments, the antiviral agent(s) is abacavir, acyclovir, acyclovir, adefovir, amantadine, amprenavir, ampligen, arbidol, atazanavir, atripla, boceprevir, cidofovir, combivir, complera, darunavir, delavirdine, didanosine, docosanol, dolutegravir, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir, peginterferon alfa-2a, penciclovir, peramivir, pleconaril, podophyllotoxin, raltegravir, ribavirin, rimantadine, ritonavir, pyramidine, saquinavir, stavudine, stribild, tenofovir, tenofovir disoproxil, tenofovir alafenamide fumarate, tipranavir, trifluridine, trizivir, tromantadine, truvada, valaciclovir, valganciclovir, vicriviroc, vidarabine, viramidine, zalcitabine, zanamivir, zidovudine, and combinations thereof.

A number of embodiments of the disclosure have been described. Nevertheless, it will be understood that various modifications may be made without departing from the spirit and scope of the disclosure. Accordingly, other embodiments are within the scope of the following claims.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Cells and Viruses: Vero cells were cultured in Dulbecco's modified Eagle's medium (DMEM; Lonza) supplemented with 10% FBS (FBS; Atlanta Biologicals), 1% Pen/Strep, and 1% HEPES. The ZIKV strains PRVABC$_{59}$, MR-766, DakAr and P6-740 were used. ZIKV infection experiments were conducted under biosafety level 2+ (BSL2+).

Peptides: Peptides were originally isolated from frogs in the Western Ghats regions of South India by stimulus driven secretion and characterized as described Reshmy, et al., *J Pept Sci* 17, 342-347, (2011). Peptides were synthesized at Genemed Synthesis Inc. (San Francisco, CA), Neo Scientific and Dr. Brian Evavold's laboratory at Emory University. As control, OVA257-264 peptide (Invivogen) was used.

Focus forming assay: Peptides were incubated with ZIKV (100 FFU/well) for 2 hours at 37° C. This incubated mixture was used to infect Vero cells for 1.5 hour at 37° C. Cells and inoculum were overlaid with 2% methylcellulose solution (OptiMEM; Gibco) and incubated for 72 hours at 37° C. Cells were washed with PBS and fixed with a 1:1 methanol/acetone mixture for 30 min. Cells were blocked with 5% milk/PSB at room temperature for 20 min and incubate with primary antibody (anti-flavivirus mouse 4G216 antibody) for 2 hours at 37° C. Then, cells were incubated with secondary antibody (HRPconjugated goat anti-mouse IgG, Cell Signaling) for 1 hour at 37° C. Cells were developed with TrueBlue Peroxidase Substrate (KPL). Plates were read on a CTL-ImmunoSpot S6 Micro analyzer.

Hemolysis toxicity assay: Single donor human red blood cells (Innovative Research) were washed in PBS (pH 7.4) with 3 times centrifugation at 500×g for 5min. Serially diluted frog peptides or OVA control peptide were prepared in V-bottom 96 well plates and mixed with washed $2\times10^7$ hRBC per each well for 1 hour at 37° C. PBS solution was used as a negative control (0% lysis) and 0.1% Triton X-100 in PBS was used as 100% lysis. The plates were centrifuged at 300×g at 4° C. for 5 minutes to pellet the intact RBCs and supernatant of each well was measured by absorbance at 450 nm.

Immunofluorescence: Vero cells were grown and infected with ZIKV (PRVABC$_{59}$) at an MOI of 1 on glass coverslips for 30 minutes and washed three times with phosphate-buffered saline (PBS) prior to fixation. Cells were then fixed with 4% paraformaldehyde solution for 10 minutes and permeabilized in 0.2% Triton X-100 for 12 minutes at room temperature. Cells were blocked in protein Block Solution Serum-Free (Dako) for 1 hour and stained with primary (mouse 4G2 monoclonal antibody and rabbit anti-alpha tubulin polyclonal antibody, Millipore) and secondary (donkey anti-mouse Alexa-488 and Alexa-594, Thermo Fisher). After wash, samples were mounted with ProLong™ Gold with DAPI (Thermo Fisher). Images were taken with an Olympus Fluoview FV1000 microscope using FV10-ASW2.1 software.

qRT-PCR: Total RNA was extracted from mock- or ZIKV-infected Vero ($2\times10^5$ cells per sample) using the RNeasy Plus mini kit (Qiagen). For qRT-PCR, total RNA was converted to complementary DNA using the High-Capacity cDNA Reverse Transcription Kit (Applied Biosystems) using random hexamers. For quantification of viral RNA, qRT-PCR was performed using TaqMan Gene Expression Master Mix (Applied Biosystems) by the manufacturer's instructions. Primers used for RT-PRC were described previously by Quicke et al. 25 Viral RNA was normalized to cellular GAPDH and relative to mock infection controls.

ZIKV negative staining for EM: ZIKV samples were fixed with 4% buffered paraformaldehyde before negative staining. 5 μL of Zika sample was then deposited onto a 400 mesh carbon coated copper grid that had been treated by glow-discharged for 20 seconds, and allowed 5 minutes for the sample to settle in a covered glass dish. Grid with sample were then quickly washed by touching the sample side on 2 drops double distilled water, wick with filter paper, and then stained with 1% phosphotungstic acid (PTA) for 15 seconds before removing PTA with filter paper. Zika virus was imaged on a JEOL JEM-1400 transmission electron microscope (JEOL Ltd., Tokyo, Japan) equipped with a Gatan US1000 CCD camera (Gatan, Pleasanton, Calif.).

Yodha Peptide and Variants are Virucidal for Zika Viruses

Figure 1B:
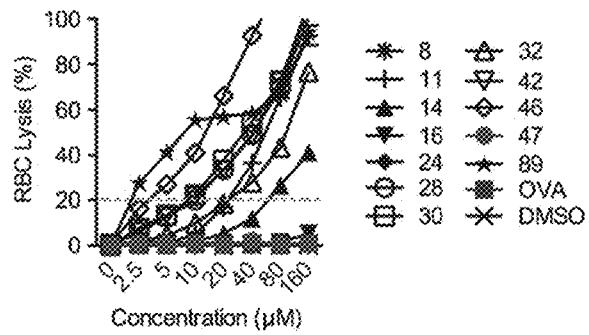
FIG. 1B. The cytotoxicity of each peptide was tested using hemolysis. Briefly, $2\times10^7$ Human red blood cells were treated with increasing concentrations of each peptide and RBC lysis.
Figure 1C:
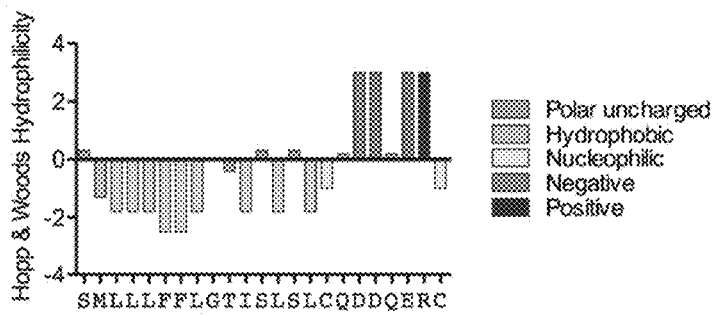
FIG. 1C. Shows the amino acid sequence (SEQ ID NO: 1) of Yodha peptide (Brevenin superfamily), represented by the Hopps & Woods amino acid hydrophilicity scale.

Frog skin peptides were screened to identify peptides with potentially virucidal activity against ZIKV infection. Individual peptides were incubated with ZIKV (PRVABC$_{59}$ strain) for 2 hours and then tested viral viability in a focus-forming assay. Of the library of 76 peptides, 12 peptides decreased ZIKV infectivity (FIG. 1A). A major drawback of host defense peptides is that they can be toxic to mammalian cells. To identify non-toxic candidates among the 12 peptides, the toxicity of each peptide were measured against human erythrocytes. Only one of the 12 peptides showed no cytotoxicity even at high concentrations (FIG. 1B). This peptide was named Yodha, which in Sanskrit means 'warrior'. The Yodha peptide, contains 23 amino acids and is provided as SMLLLFFLGTIS-LSLCQDDQERC (SEQ ID NO:1) and belongs to the Brevenin superfamily. This peptide was analyzed using the Hopp and Woods plot (Hopp et al. P Natl Acad Sci-Biol 78, 3824-3828, (1981)) and interestingly, amino acids with hydrophobic side chains dominate almost half of the N-terminal region of Yodha peptide (FIG. 1C). The C-terminus of Yodha peptide contains 3 negatively charged amino acids ((Asp(D) and Glu(E)).

Figure 1D:
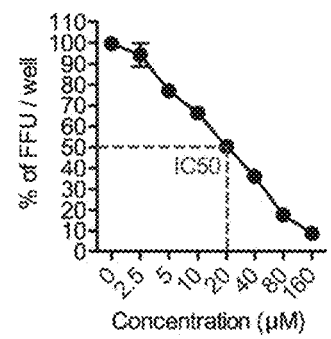
FIG. 1D. Shows $IC_{50}$ measurement of Yodha peptide in ZIKV infection by FFA. Data are means±SEM from at least three independent experiments.
Figure 1E:
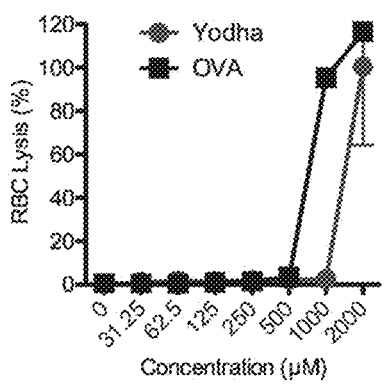
FIG. 1E. The cytotoxicity of Yodha peptide and OVA peptide were tested using higher concentrations of up to 200 µM against human RBCs. Human red blood cells were treated with increasing concentrations of each peptide and RBC lysis.
Figure 1F:
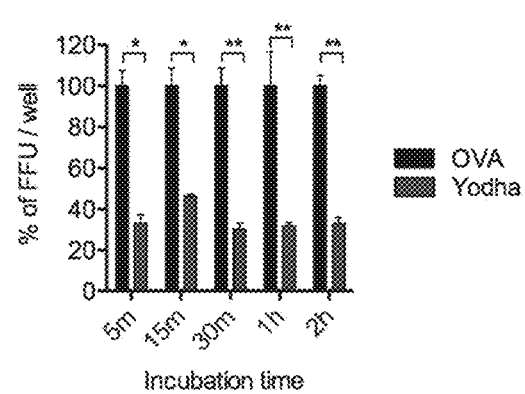
FIG. 1F. The kinetics of Yodha peptide induced ZIKV inhibition was examined over time (5 minutes to 2 hours) (peptide concentration 20 µM). OVA peptide used as a positive control (set as a 100% of FFU/well). Values represent mean±S.E.M. *P<0.05 and **P<0.01; by Two-way ANOVA.

To determine the half-maximal inhibitory concentration ($IC_{50}$), a dose escalation analysis of the Yodha peptide (2.5 μM to 160 μM) was performed against ZIKV and observed 35%, 50%, 65%, 80%, and 90% reductions at 10 μM, 20 μM, 40 μM, 80 μM, and 160 μM, respectively. The $IC_{50}$ of Yodha peptide is 20 μM(FIG. 1D). To determine the maximum concentration of Yodha that could be used without toxicity, the human red blood cell (RBC) cytotoxicity test was conducted at peptide concentrations ranging from 31.25 μM to 2000 μM. Yodha was non-toxic even at 1000 μM and showed toxicity only at 2000 μM (FIG. 1E). The kinetics of viral reduction by this peptide following exposure to ZIKV was also determined. ZIKV was exposed to Yodha peptide for 5 min, 15 min, 30 min, 1 hour, and 2 hours. Viral titers (measured as Focus Forming Unit, FFU) were significantly decreased at all time points tested, and strongly indicates that the maximum activity of the Yodha peptide occurs within the first five minutes of incubation with ZIKV (FIG. 1F).

ZIKV can be divided into four distinct lineages based on sequence homology (Petersen et al. *N Engl J Med* 375, 294-295, (2016); Hamel et al. *Microbes Infect* 18, 441-449, (2016)). The first ZIKV, MR-766 was isolated in Uganda from a sentinel rhesus monkey in 1947. In 1966, the first non-African strain P6-740 was isolated in Malaysia from a pool of *Aedes aegypti* mosquitoes. The African strain, DaKar41524 was isolated from a pool of *Aedes africanus* mosquitoes from Senegal in 1984. In 2015, the contemporary strain, PRVABC$_{59}$, was isolated in Puerto Rico from an infected human patient. This strain, which is closely related to the epidemic strains circulating in the Americas have been linked to in utero ZIKV infection. All the experiments in FIGS. 1A-1F, used the PRVABC$_{59}$ (Puerto Rico 2015) strain of ZIKV.

Figure 2A:
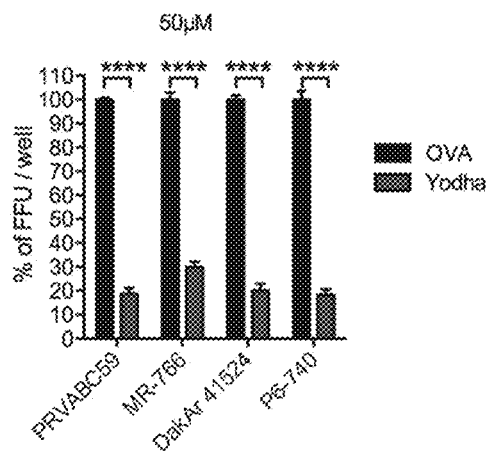
FIG. 2A. Shows data indicating Yodha peptide inhibits all 4 strains of ZIKV. Zika virus strains PRVABC59, MR-766, DakAr 41524, and P6-740 were exposed to Yodha or control OVA peptide at 50 µM. Values represent mean±S.E.M. ****p<0.0001; by Two-way ANOVA.
Figure 2B:
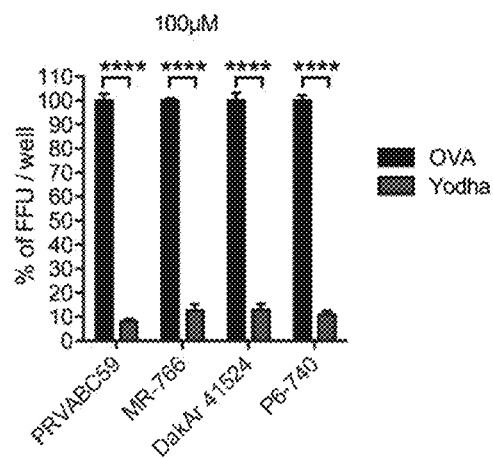
FIG. 2B. Shows data at 100 µM.

Next, the extent to which Yodha peptide would inhibit the different strains of ZIKV, MR-766 (Uganda, 1947), DakAr41524 (Senegal 1984), P6-740 (Malaysia, 1966) and PRVABC$_{59}$ (Puerto Rico, 2015) were determined. The Yodha peptide inhibited all ZIKV strains (FIGS. 2A and 2B). Taken together, the data suggests that Yodha peptide might target a common region that is shared by ZIKV.

Figure 3A:
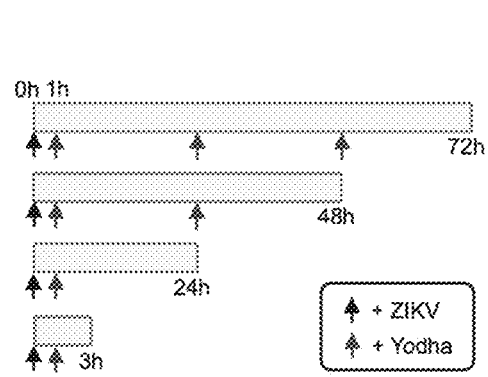
FIG. 3A. Shows treatment with Yodha peptide decreases ZIKV replication in vitro as a schematic of an experimental design. Vero cell monolayers were infected first with ZIKV and then treated with Yodha peptide or control OVA peptides (40 µM) at 1 h, 24 h, 48 h and 72 h post-infection. Culture supernatants were harvested at 3, 24, 48, and 72 hours post infection and assayed for ZIKV.
Figure 3B:
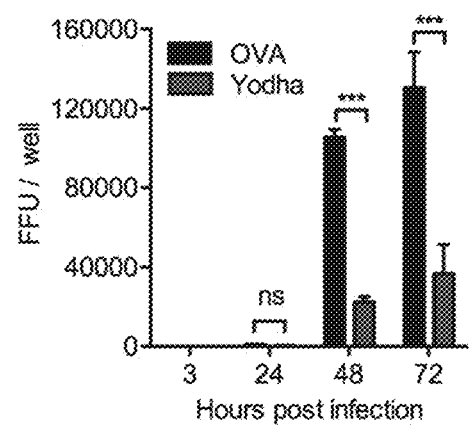
FIG. 3B. Shows treatment with Yodha peptide led to significantly reduced ZIKV titers in the supernatants. Error bars indicate the SEM of four technical replicates statistical significance was assessed by a 2-way ANOVA.

Also determined was whether Yodha peptide could reduce infectious virus production in cells already infected with ZIKV. Briefly, Vero cells were infected, allowed virus attachment and entry and then Yodha peptide was added to the culture medium at 1, 14, 48, and 72 hours post-infection. Culture supernatants at 3, 24, 48, and 72 hours after ZIKV infection were collected to quantitate ZIKV by FFU assay (FIG. 3A). ZIKV was not detected at 3 hours post-infection in both OVA- or Yodha peptide treated cells. A 60-70% reduction in ZIKV production at 48 and 72 hours post-infection was observed (FIG. 3B). Taken together the data shows that Yodha peptide can significantly reduce viral titers and limit the spread of ZIKV in vitro.

Figure 4A:
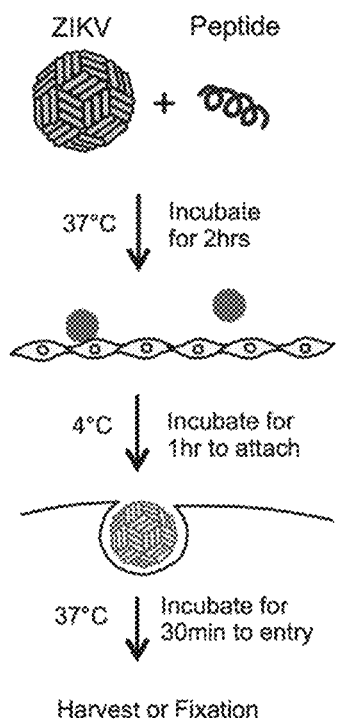
FIG. 4A. Illustration a schematic diagram of the experimental setup to show Yodha peptide inhibits ZIKV entry into cells.
Figure 4B:
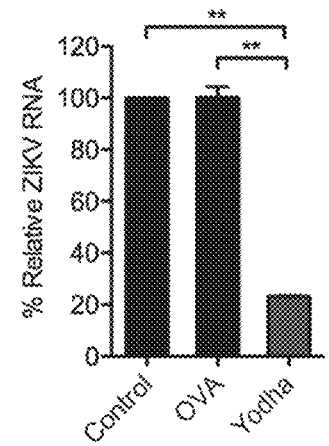
FIG. 4B. Shows ZIKV treated with 200 µM of Yodha peptide or control OVA peptide for 30 min and then used to infect Vero cells at a MOI of 0.5 and expression of ZIKV RNA was determined by quantitative RT-PCR (qRT-PCR). Cellular glyceraldehyde-3-phosphate dehydrogenase (GAPDH) served as internal control. T-test two tailed (**) p=0.0028.
Figures 4C, 4D, 4E:
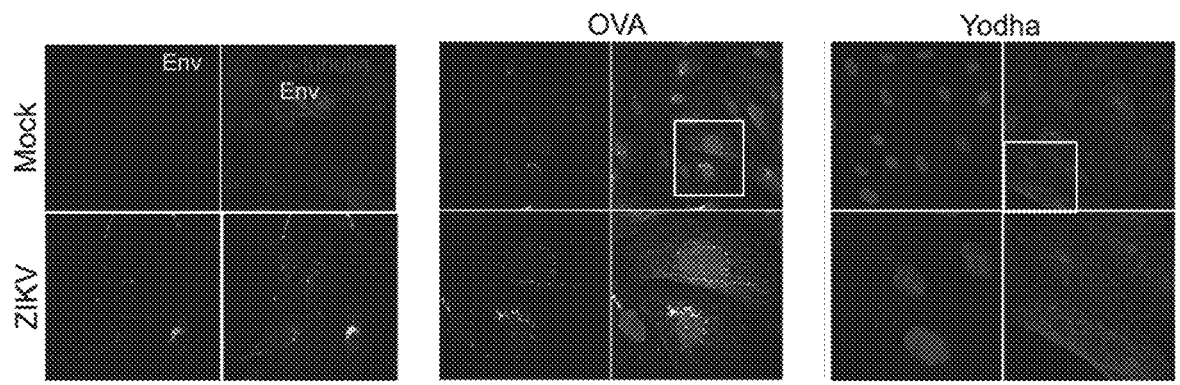
FIG. 4C. Shows mock-infected and ZIKV-infected Vero cells were fluorescently stained for ZIKV envelope (green), a-tubulin (red) and DAPI (blue).
FIG. 4D. Shows ZIKV exposed to control ova peptide or Yodha peptide.
FIG. 4E. Shows the sample from FIG. 4D when then used to infect Vero monolayers. ZIKV envelope was visible inside the cytoplasm in control but not Yodha-peptide treated Vero cells.

Next, whether the observed Yodha peptide-induced decrease in viral titers was due to blocked viral entry was determined. It was reasoned that if the peptide directly kills or disrupts the envelope structure of ZIKV, this would prevent virus entry. To test this, an experiment to measure virus entry by allowing ZIKV to bind cells at 4° C. for 1 hour followed by shifting the cells to 37° C. to permit virus entry was carried out (FIG. 4A). It has been shown that DENV2 entry occurs within 25 min by early endosome trafficking (Ang et al. *Virol J* 7, 24, (2010)). ZIKV was exposed to Yodha peptide and then the virus was allowed to infect Vero cells for 30 mins. The viral RNA within the Vero cells (FIG. 3A) was measured by quantitative Real Time-PCR (qRT-PCR) (FIG. 4B). Comparable amounts of ZIKV RNA were detected in the virus-only samples and control samples of ZIKV incubated with control OVA peptide. It was shown that cells infected with ZIKV that were pre-incubated with Yodha peptide had only 20% of the ZIKV RNA expressed compared to the OVA and virus-only controls, suggesting that exposure to Yodha peptide significantly reduced the ability of ZIKV to enter the host cells. Next, ZIKV entry or lack thereof was visualized by immunofluorescence using antibodies against pan flavivirus E protein (FIG. 4C). As expected from the qRT-PCR results, decreased expression of ZIKV envelope in Yodha peptide-treated samples (FIG. 4E) was observed, while the OVA control (FIG. 4D) showed no such effect. This suggests that Yodha peptide inhibits ZIKV and prevents viral entry into cells.

Figure 5A:
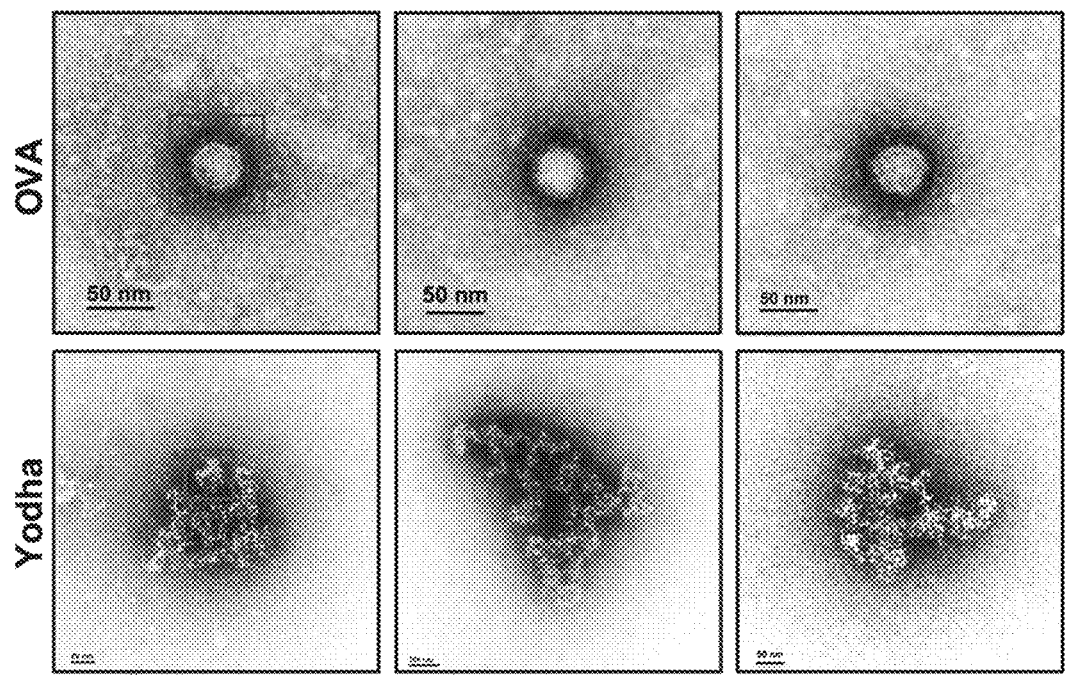
FIG. 5A. Transmission electron microscopy micrographs showing that Yodha peptide destroys ZIKV. TEM micrographs of ZIKV treated with OVA peptide (control) or Yodha peptide. ZIKV was incubated with the peptides at 200 µM for just 10 minutes, fixed with paraformaldehyde and then processed for electron microscopy. Yodha peptide treatment led to loss of morphology and aggregation of virus particles.
Figure 5B:
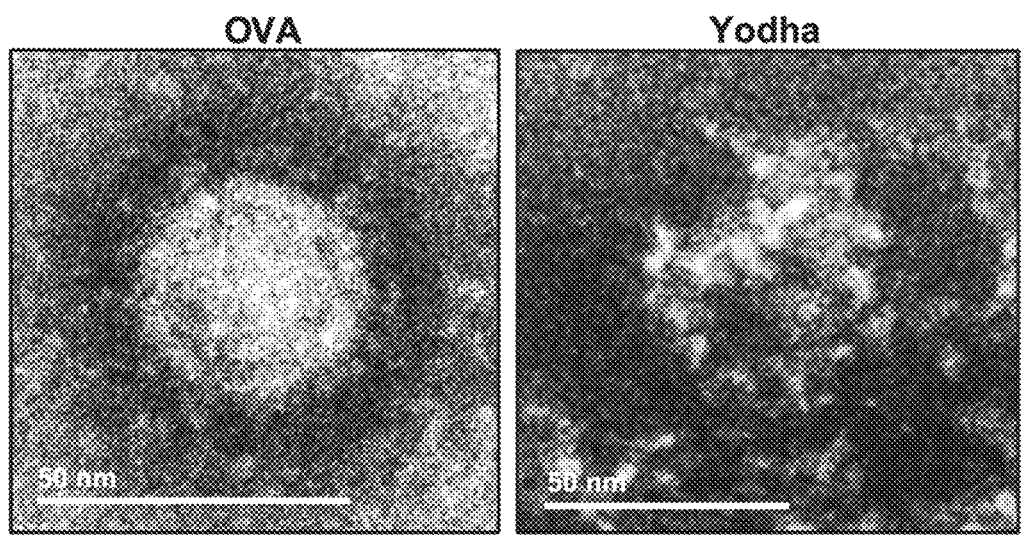
FIG. 5B. Enlarged images of ZIKV treated with control or Yodha peptide from (5A). The data is representative of three experiments performed.

FIGS. 4A-4E show that exposure of ZIKV to Yodha peptide inhibited viral entry and this effect could be due to peptide binding to the virus and blocking entry or, alternatively, the peptide could be destroying the virus. To test this, ZIKV was treated with Yodha peptide or control peptide for 10 mins and was then analyzed by electron microscopy. Surprisingly, a 10-min treatment with Yodha peptide induced disruption of viral particles in contrast to the control peptide treated ZIKV, which exhibited intact virions (FIGS. 5A and 5B). ZIKV treated with Yodha peptide exhibited significant structural disruption, as seen by the loss of a well-circumscribed morphology, loss of clearly defined layers, and formation of aggregates composed of disrupted viral particles—a feature that has also been observed in defensin-induced viral aggregation (Doss et al. *Protein D. J Immunol* 182, 7878-7887, (2009); Doss et al. *J Immunol* 188, 2759-2768, (2012)). Taken together, these results indicate that ZIKV treated with Yodha peptide loses its infectivity due to physical disruption of the Zika virion.

To further characterize Yodha peptide, alanine-scanning mutants of the peptide were generated, which remove the side chain but maintain peptide conformation, allowing for the assessment of the significance of each amino acid within the larger structure (FIG. 6A). Each of 23 mutated peptides (SEQ ID NOS:2-24) was tested for its (a) ability to neutralize ZIKV (FIG. 6B) and (b) toxicity against human RBC, if any (FIG. 6C). Interestingly, only one of the alanine mutants (peptide 8) showed statistically significant (p=0.02) antiviral activity than the parental peptide while 20 out of 23 mutants had decreased activity and two mutants exhibited comparable activity as Yodha peptide (FIG. 6B). None of the ALA mutants were toxic and caused lysis of RBCs (FIG. 6C). Chirality is an important factor to consider for pharmacological application, since the mirror-image, D-enantiomer peptide is more stable in vivo that the naturally occurring L-enantiomer. Both D- and L-form of peptide neutralized ZIKV with comparable efficiency (FIG. 6D) suggesting that this peptide might target a symmetric structure in the virus that is recognized by both D and L form of peptide.

The *Hylarana aurantiaca* South Indian-frog produces Yodha peptide almost certainly not to specifically fight Zika viruses but to combat other pathogen(s) it would encounter in its niche. It was determined how common this peptide or its analogues are in host defense peptides isolated from elsewhere in the world. The BLASTp program was searched and 31 peptides were identified that exhibited high levels of homology especially in the hydrophobic N-terminus (FIG. 7A). (SEQ ID NOS: 25-55) The extent to which any of these variant peptides can neutralize ZIKV was determined.

First, their toxicity was determined and none of these variant peptides showed toxicity to human RBCs (FIG. 7B). All of the variant peptides except one showed virucidal activity against ZIKV (FIG. 7C); variant 25 (SEQ ID NO:49), which is identical to Yodha except for the 6 C terminal amino acids exhibited no virucidal effect on the virus. On the other hand, variant 12 (SEQ ID NO:36) (brevinin-2KK2 from (*Rana kukunoris*), PMLLLFFLGTIS-LSLCQEEERGA), demonstrated 1.6-fold increased effect against ZIKV than Yodha peptide. On the N-terminus, Yodha peptide and variant 12 (SEQ ID NO:36), are identical except for position 1, which is changed from a Serine to a Proline residue; the C terminus of these peptides differ after position 17(Q). Variant 21 (SEQ ID NO:45) (PMLLLFFLG-TISLSLCQEERGA) which was isolated from the frog, *I. temporalis* hailing from the same geographical area as the Yodha peptide-expressing frog *Hyalarana aurantiaca*, presented the S1-P change but had one less glutamic acid amino acid at the terminus also exhibited activity against ZIKV.

Next investigated was whether the S to P change at position 1 or removing the C terminus (sequences after Q17) contributes to the improved activity. Also generated was a truncated, short Yodha peptide (SEQ ID NO:56) that removed C terminal DDQERC (SEQ ID NO: 81) from Yodha, Short 12 peptide (SEQ ID NO:57) that removed EEERGA (SEQ ID NO: 82) from variant 12, and S 1P Yodha (SEQ ID NO:58) that replace S1-P in full length Yodha (FIG. 7D). These were tested for activity against ZIKV (FIG. 7D). S 1P full length Yodha peptide was significantly more effective against ZIKV than the WT Yodha peptide. Removal of the C terminus from Yodha as well as variant 12 (SEQ ID NO:36) significantly improved activity. This also suggests that the activity lies in the N terminal hydrophobic region. Taken together, these results suggest that either changing S-P at position 1 at the N terminus or removing the C terminal end—DDQERC (SEQ ID NO: 81) improves activity of the Yodha peptide against Zika viruses.

TABLE 3

Yodha polypeptides, mutants, and variants thereof.

| SEQ ID NOs | Source | Amino acid Sequence |
|---|---|---|
| SEQ ID NO: 1 (Yodha) | Hylarana aurantiaca | SMLLLFFLGTISLSLCQDDQERC |
| SEQ ID NO: 2 | Alanine-scanning mutants 1 | AMLLLFFLGTISLSLCQDDQERC |
| SEQ ID NO: 3 | Alanine-scanning mutants 2 | SALLLFFLGTISLSLCQDDQERC |
| SEQ ID NO: 4 | Alanine-scanning mutants 3 | SMALLFFLGTISLSLCQDDQERC |
| SEQ ID NO: 5 | Alanine-scanning mutants 4 | SMLALFFLGTISLSLCQDDQERC |
| SEQ ID NO: 6 | Alanine-scanning mutants 5 | SMLLAFFLGTISLSLCQDDQERC |

TABLE 3-continued

Yodha polypeptides, mutants, and variants thereof.

| SEQ ID NOs | Source | Amino acid Sequence |
|---|---|---|
| SEQ ID NO: 7 | Alanine-scanning mutants 6 | SMLLLAFLGTISLSLCQDDQERC |
| SEQ ID NO: 8 | Alanine-scanning mutants 7 | SMLLLFALGTISLSLCQDDQERC |
| SEQ ID NO: 9 | Alanine-scanning mutants 8 | SMLLLFFAGTISLSLCQDDQERC |
| SEQ ID NO: 10 | Alanine-scanning mutants 9 | SMLLLFFLATISLSLCQDDQERC |
| SEQ ID NO: 11 | Alanine-scanning mutants 10 | SMLLLFFLGAISLSLCQDDQERC |
| SEQ ID NO: 12 | Alanine-scanning mutants 11 | SMLLLFFLGTASLSLCQDDQERC |
| SEQ ID NO: 13 | Alanine-scanning mutants 12 | SMLLLFFLGTIALSLCQDDQERC |
| SEQ ID NO: 14 | Alanine-scanning mutants 13 | SMLLLFFLGTISASLCQDDQERC |
| SEQ ID NO: 15 | Alanine-scanning mutants 14 | SMLLLFFLGTISLALCQDDQERC |
| SEQ ID NO: 16 | Alanine-scanning mutants 15 | SMLLLFFLGTISLSACQDDQERC |
| SEQ ID NO: 17 | Alanine-scanning mutants 16 | SMLLLFFLGTISLSLAQDDQERC |
| SEQ ID NO: 18 | Alanine-scanning mutants 17 | SMLLLFFLGTISLSLCADDQERC |
| SEQ ID NO: 19 | Alanine-scanning mutants 18 | SMLLLFFLGTISLSLCQADQERC |
| SEQ ID NO: 20 | Alanine-scanning mutants 19 | SMLLLFFLGTISLSLCQDAQERC |
| SEQ ID NO: 21 | Alanine-scanning mutants 20 | SMLLLFFLGTISLSLCQDDAERC |
| SEQ ID NO: 22 | Alanine-scanning mutants 21 | SMLLLFFLGTISLSLCQDDQARC |
| SEQ ID NO: 23 | Alanine-scanning mutants 22 | SMLLLFFLGTISLSLCQDDQEAC |
| SEQ ID NO: 24 | Alanine-scanning mutants 23 | SMLLLFFLGTISLSLCQDDQERA |
| SEQ ID NO: 25 | Variant 1 | SMLLLFFLGTISLSLCQDERGA |
| SEQ ID NO: 26 | Variant 2 | SMLLLFFLGTISLSLCQDEGA |
| SEQ ID NO: 27 | Variant 3 | SMLLLFFLGTISLSLCQEEERGA |
| SEQ ID NO: 28 | Variant 4 | SMLLLFFLGTISLSLCEQERNA |
| SEQ ID NO: 29 | Variant 5 | SMLLLFFLGTISLSLCEQERDSD |
| SEQ ID NO: 30 | Variant 6 | SMLLLFFLGTISLSLCEQERDAD |
| SEQ ID NO: 31 | Variant 7 | SMLLLFFLGTISLSLCQEERGA |
| SEQ ID NO: 32 | Variant 8 | SMLLLFFLGTISLSLCEEERNA |
| SEQ ID NO: 33 | Variant 9 | SMLLLFFLGTISLSLCQEERDA |
| SEQ ID NO: 34 | Variant 10 | SLLLLFFLGTISLSLCQDETNA |
| SEQ ID NO: 35 | Variant 11 | SLLLLFFLGTINLSLCQDDEMPK |
| SEQ ID NO: 36 | Variant 12 | PMLLLFFLGTISLSLCQEEERGA |
| SEQ ID NO: 37 | Variant 13 | SMLLLFFLGTINLSLCQEERDA |
| SEQ ID NO: 38 | Variant 14 | SLLLLFFLGTISLSLCQEEERNA |
| SEQ ID NO: 39 | Variant 15 | SMLLLFFLGMISLSLCQDERGA |
| SEQ ID NO: 40 | Variant 16 | MLLLFFLGTISLSLCEQERNA |
| SEQ ID NO: 41 | Variant 17 | SMLLLFFLGTINLSLCEQERDA |
| SEQ ID NO: 42 | Variant 18 | PMLLLFFLGTISLSLCEQERNA |
| SEQ ID NO: 43 | Variant 19 | SMLLLFFLGTINLSLCEQERNA |
| SEQ ID NO: 44 | Variant 20 | SLLLLFFLGTISLSLCQREAD |
| SEQ ID NO: 45 | Variant 21 | PMLLLFFLGTISLSLCQEERGA |
| SEQ ID NO: 46 | Variant 22 | SLLLLFFLGTINLSLCQDETNA |
| SEQ ID NO: 47 | Variant 23 | SMLLLFFLGTINLSLCEEERDA |
| SEQ ID NO: 48 | Variant 24 | SMLLLFFLGTISLSLCEEER |
| SEQ ID NO: 49 | Variant 25 | SMLLLFFLGTISLSLCEEERDA |
| SEQ ID NO: 50 | Variant 26 | SMLLLFFLGTISLSLCEEERSA |
| SEQ ID NO: 51 | Variant 27 | SMLLLFFLGTISLSLCEEERNA |
| SEQ ID NO: 52 | Variant 28 | SMLLLFFLGTISLSLCEEERGA |
| SEQ ID NO: 53 | Variant 29 | SMLLFFFLGTISLSLCQEEERGA |
| SEQ ID NO: 54 | Variant 30 | SLLLLFFLGTISLSLCEEERNA |
| SEQ ID NO: 55 | Variant 31 | SMLLI FFLGTISLSLCEQERDA |
| SEQ ID NO: 56 | Short Yodha | SMLLLFFLGTISLSLCQ |
| SEQ ID NO: 57 | Short Yodha12 | PMLLLFFLGTISLSLCQ |
| SEQ ID NO: 58 | SIP Yodha | PMLLLFFLGTISLSLCQDDQERC |

Host defense peptides, which constitute the ancient arm of the innate immune system confers protection to the host. The amphibian host defense peptide Yodha acts against Zika viruses. This peptide and variants thereof can be used as antivirals for at least the following reasons. First, they can act on the virus directly and cause lysis of the virus. Second, Yodha peptide acts on all lineages of ZIKV. Each of the four ZIKV strains were independently sequenced and found that P6-1966, MR-1947, and Dak-194 differed at the amino acid level from PR-2015 by 1.1%, 3.2%, and 3.0%, respectively. Also, MR-1947 diverged from PR-2015 more notably in the structural (4.4%) than non-structural proteins (2.9%). Nonetheless, Yodha peptide targets all four different lineages suggesting that it may be targeting a motif that is conserved among all ZIKV. Third, Yodha peptide is nontoxic to human RBC; the $IC_{50}$ of this peptide is 20 μM (0.052 mg/mL) and non-toxic at 1000 μM (2.6 mg/ml) giving a large range of doses that can be administered. Fourth, Yodha peptide rapidly neutralizes the virus, at least within 5 minutes of exposure to virus, which is an advantageous feature in a therapeutic. Fifth, it was shown that both L- and D-enantiomeric forms of Yodha peptides work against ZIKV (FIG. 2D) and this is significant because unlike the naturally occurring L-form, the D-form is more stable in vivo as is less susceptible to endogenous proteases.

It is unclear what part of ZIKV the Yodha peptide targets. Since it is effective against ZIKV viruses that circulated over a span of 68 years (1947-2015), it is likely that the peptide targets some motif that is conserved among all of these viruses. EM studies showed that the Yodha peptide induces viral lysis. Hydrophobicity has been known to be the main driving force for the integration of transmembrane segments into the lipid bilayer of the protein. Interestingly the Yodha peptide as well as the naturally occurring variant peptides shown in FIGS. 7A-7F have a common hydrophobic N terminus (FIG. 1C) to which the activity of the peptide could be mapped to. This suggests that the peptide perhaps destabilizes the virus by integrating into the viral lipid bilayer using the hydrophobic N-terminus.

Naturally occurring variants of the Yodha peptide are also active against ZIKV. These peptides came from frogs with natural habitats that span the globe—India, China, Sri Lanka, Myanmar, USA, Canada, Mexico, Korea, Russia and Europe. It is highly unlikely that these amphibians produce these peptides to combat ZIKV but instead, these peptides confer survival advantage against some common amphibian pathogen. These peptides might act via "pattern recognition" analogous to toll like receptors and the ZIKV happen to share these patterns/motifs. These findings show that Yodha peptide can be useful as anti-viral compound to ZIKV viruses. The direct virucidal activity of this peptide on ZIKV as well as its low toxicity on human RBCs make it a candidate for combating ZIKV.

The Yodha Peptide is Efficient in Reducing Viral Titers in Mice

Figure 11A:
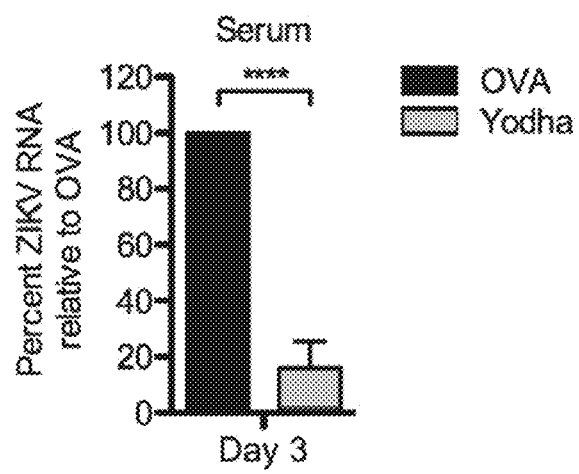
FIG. 11A. Shows viremia in the serum days 3 post-infection indicating administration of Yodha peptide reduces ZIKV viremia and viral burden in mice. Cohorts of 4-5 week-old mice were given 2 mg anti-Ifnar1 mAb intraperitoneally, and the following day infected with $10^5$ FFUs of PRVABC ZIKV. Viremia and viral burden were monitored by real time PCR.
Figure 11B:
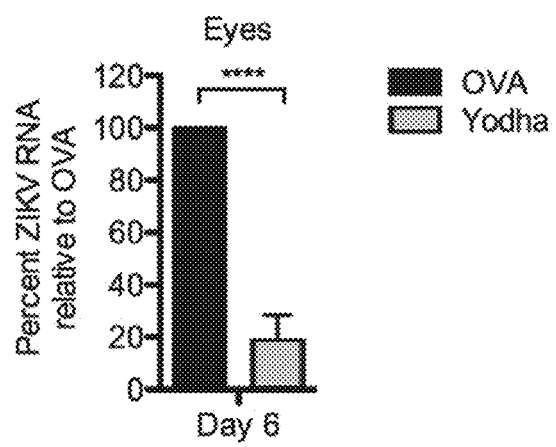
FIG. 11B. Shows viral burden at day 6 in the eye.
Figure 11C:
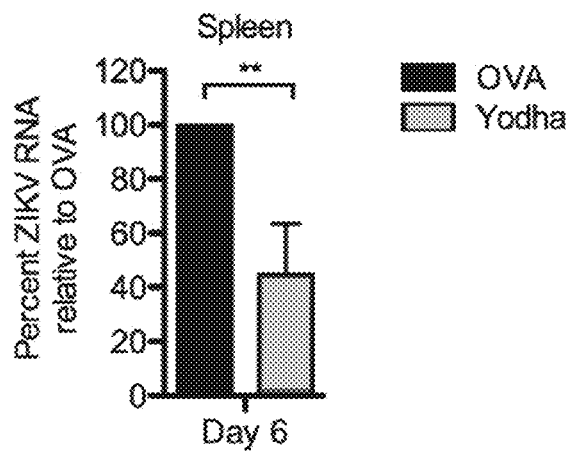
FIG. 11C. Shows viral burden at day 6 in the spleen.

Administration of Yodha peptide reduces ZIKV viremia and viral burden in mice. Cohorts of 4-5 week-old mice were given 2 mg anti-Ifnarl mAb intraperitoneally, and the following day infected with $10^5$ FFUs of PRVABC ZIKV. Viremia and viral burden were monitored in serum and tissues by real time PCR. See FIG. 11A-C.

Yodha Peptide is Virucidal for Dengue Viruses

Figure 8A:
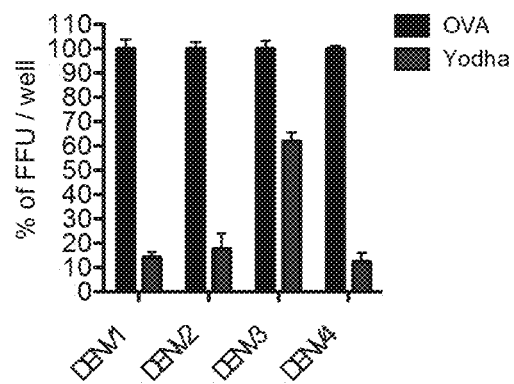
FIG. 8A. Show Yodha peptide neutralizes DENV serotypes 1, 2, 3, and 4 from Yodha peptide incubated at 50 µM and the % of viral focus forming units were determined.
Figure 8B:
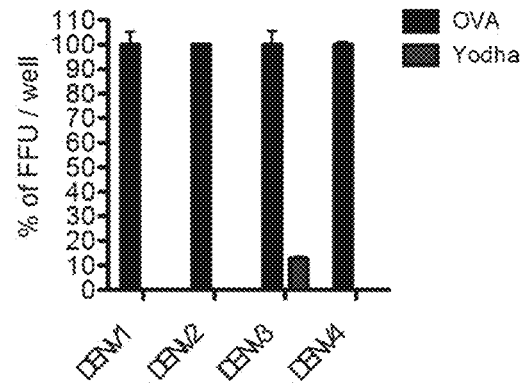
FIG. 8B. Shows results from Yodha peptide incubated at or 160 µM. The lower dose of Yodha peptide was effective against DENV 1, 2, and 4. Neutralization of DENV 3 required higher dose of Yodha peptide.
Figure 8C:
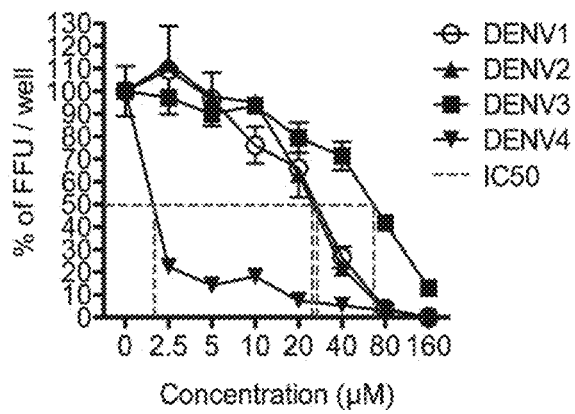
FIG. 8C. $IC_{50}$ measurement of Yodha in DENVs infection by FFA.
Figure 8D:
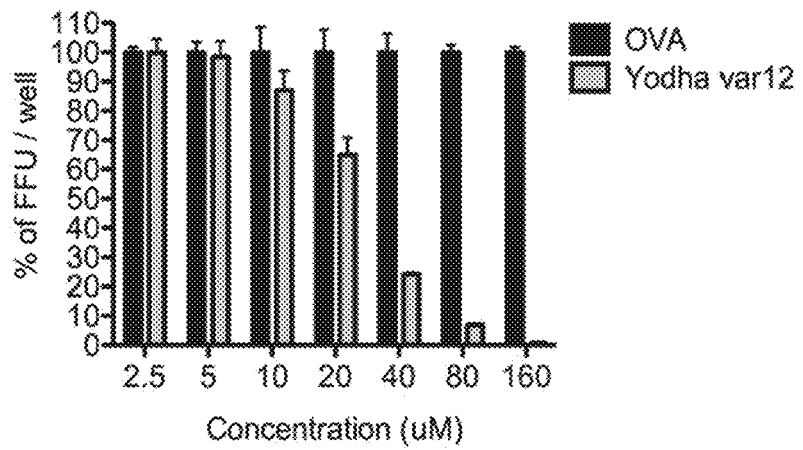
FIG. 8D. Dose escalation of truncated Yodha variant 12 against DENV3 infection shows that the truncated version is more efficient than the full-length Yodha peptide. OVA peptide was used as a negative control and was set as 100% viral FFU/well.

Dengue fever is a mosquito-borne disease that causes approximately 400 million cases worldwide. It is estimated that 3.9 billion people, in 128 countries are at risk of succumbing form Dengue. This is caused by Dengue virus which belongs to Flaviviridae, the same family of viruses as Zika. There are four serotypes of Dengue viruses, DENV 1-4. Exposure to one serotype enhances infectivity to other serotypes as antibodies made against one serotype cross reacts and binds to the other serotype and facilitates increased infection. Currently neither a vaccine nor anti-viral drugs are available against Dengue viruses. Yodha peptide was found to be virucidal for all four serotypes of Dengue viruses. Interestingly DENV 1, 2 and 4 was easily neutralized at 50 μM peptide concentration (FIG. 8A) and DENV 4 required higher dose (160 μM) of Yodha peptide to be effective (FIG. 8B). Dose escalation of truncated Yodha variant 12 against DENV3 infection shows that the truncated version is more efficient than the full length Yodha peptide (FIG. 8D)

Yodha Peptide is Virucidal for Human Influenza Viruses

Figure 9A:
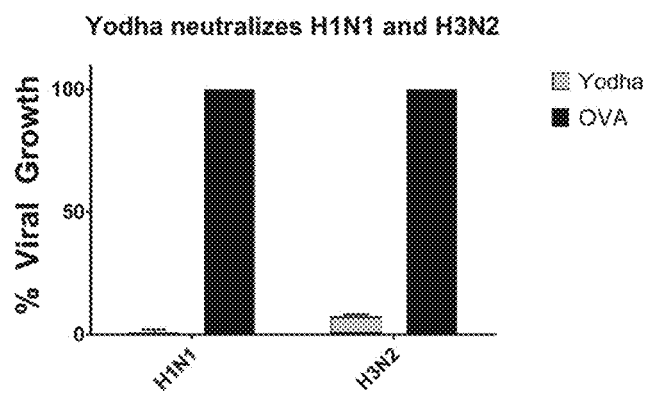
FIG. 9A. Shows Yodha peptide neutralizes H1N1 and H3N2 human influenza viruses. Yodha peptide was incubated with H1N1 and H3N2 viruses at 37° C. for 1 hour and then the virus was plated on MDCK cell monolayers. The following day virus was visualized using a focus forming assay.
Figure 9B:
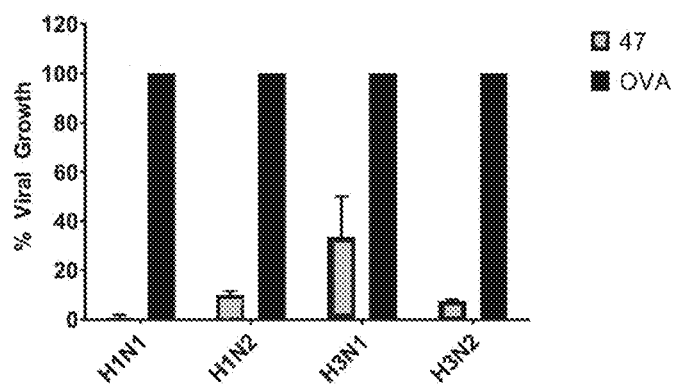
FIG. 9B. Shows Yodha peptide (47) is effective against may subtypes of influenza viruses.
Figure 9C:
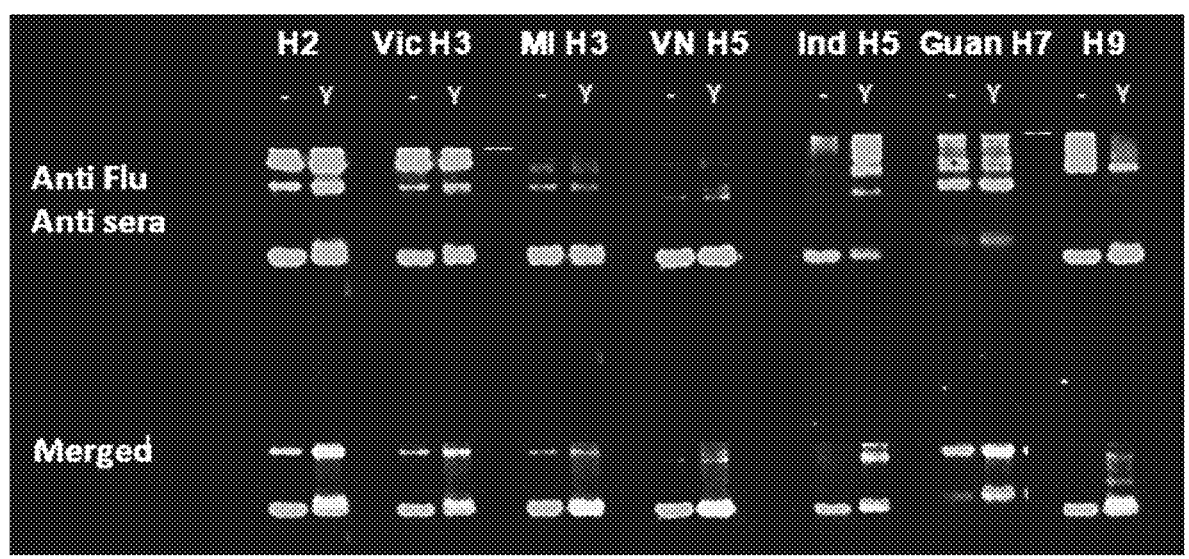
FIG. 9C. Shows data indicating that Yodha peptide binds to H2, H5, H7 and H9 avian influenza hemagglutinins.
Figure 10A:
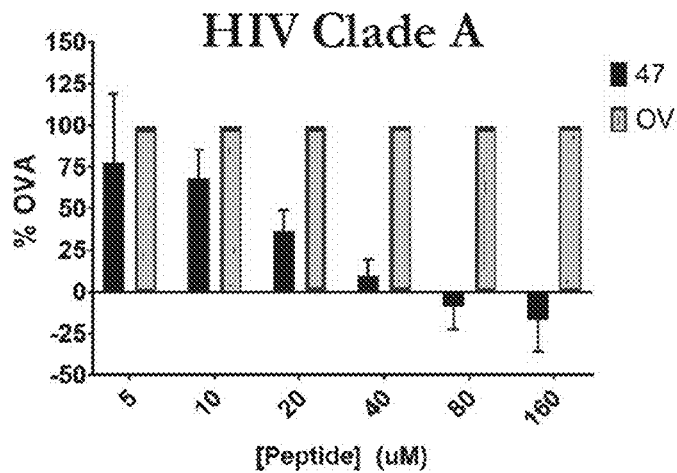
FIG. 10A. Shows 40 uM of Yodha peptide (47) efficiently inhibited claded A HIV. Clades A, B and C HIV viruses were exposed to graded doses (5 um-160 uM) of either Yodha peptide or control OVA peptide.
Figure 10B:
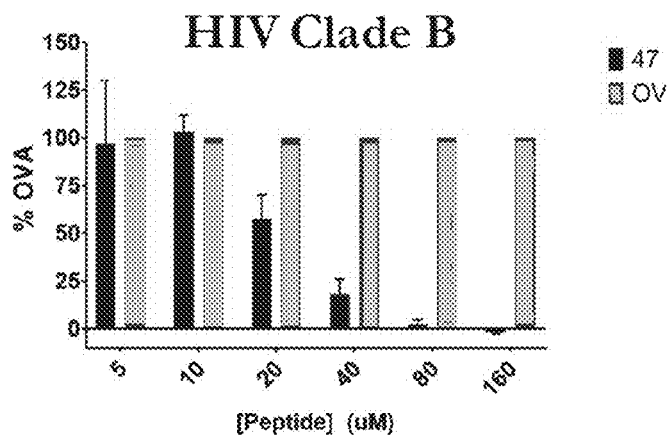
FIG. 10B. Shows 40 uM of Yodha peptide (47) efficiently inhibited claded B HIV.
Figure 10C:
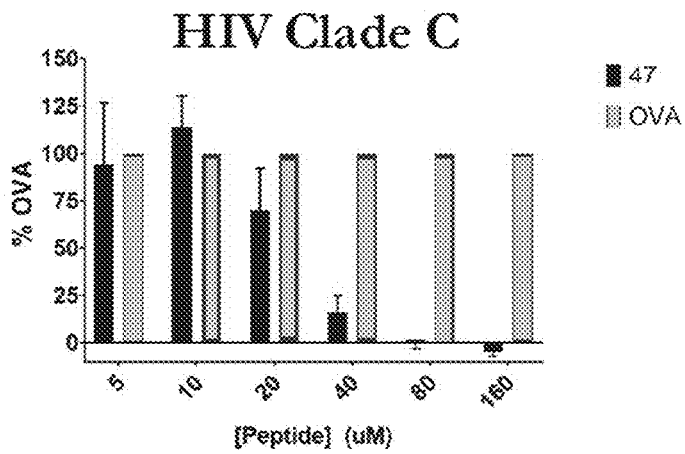
FIG. 10C. Shows 40 uM of Yodha peptide (47) efficiently inhibited claded C HIV.

Experiments were performed indicating that Yodha peptide is effective against all subtypes of influenza viruses. Yodha peptide is efficient against H1, H3, N1, N2 influenza viruses. FIG. 9A shows data indicating Yodha peptide is virucidal for H1N1, H3N2, H1N2, H3N1, and H3N2 viruses. Yodha peptide binds to H2, H5, H7 and H9 avian influenza hemagglutinins as well. Recombinant hemagglutinins from three H3 viruses and avian viruses H2, H5, H7 and H9, were incubated with biotinylated Yodha peptide. A western blot with anti-flu antisera was used to detect viral HA and streptavidin PE to detect biotinylated Yodha peptide. Yodha peptides binds to HA from the influenza viruses tested suggesting that it has broad activity against influenza viruses.

Truncation Variants of Yodha Peptide

Figure 12:
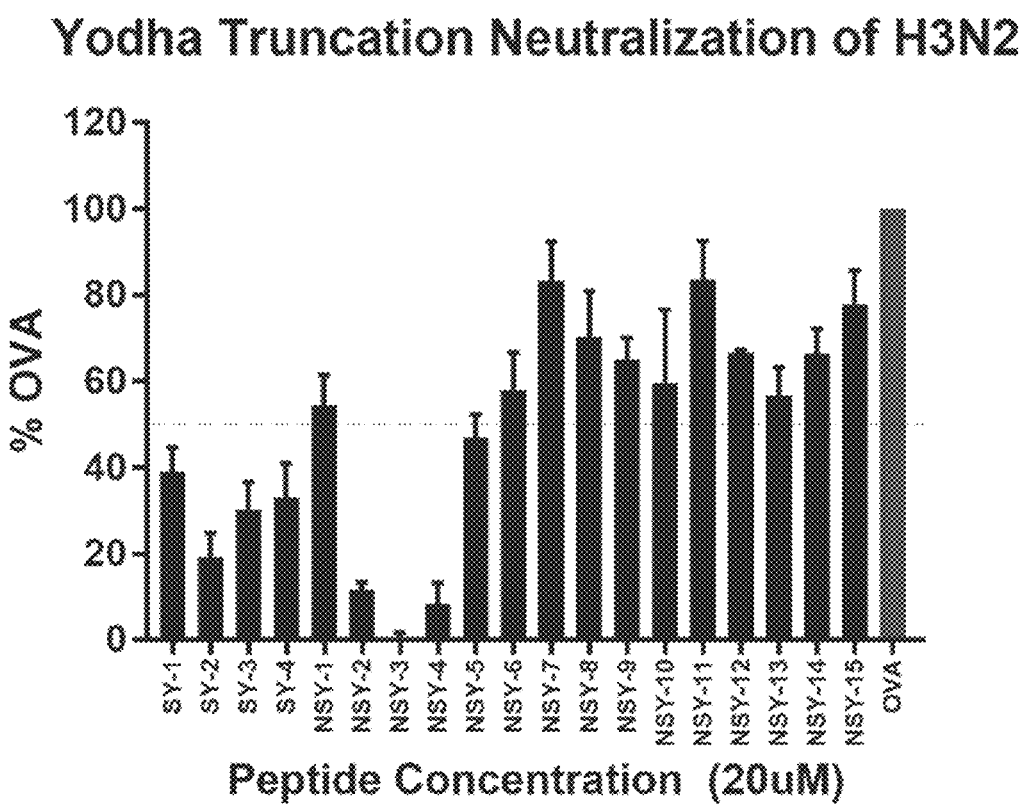
FIG. 12. Shows data indicating truncated variants of Yodha peptide neutralize H3N2 influenza.

Nested truncation variants of Yodha peptide were produced. These were incubated with H3N2 influenza (A/Aichi/2/68) and then tested in a cell-based assay for neutralization capacity relative to a control peptide. See FIG. 12. This data indicates that 8 of the 19 (42%) tested truncations neutralize 50% or more of the added H3N2.

| Sequence | Code | |
|---|---|---|
| SMLLLFFLGTISLSLCQDDQER | SY-1 | SEQ ID NO: 59 |
| SMLLLFFLGTISLSLCQDDQE | SY-2 | SEQ ID NO: 60 |
| SMLLLFFLGTISLSLCQDDQ | SY-3 | SEQ ID NO: 61 |
| SMLLLFFLGTISLSLCQDD | SY-4 | SEQ ID NO: 62 |
| MLLLFFLGTISLSLCQDDQERC | NSY-1 | SEQ ID NO: 63 |
| LLLFFLGTISLSLCQDDQERC | NSY-2 | SEQ ID NO: 64 |
| LLFFLGTISLSLCQDDQERC | NSY-3 | SEQ ID NO: 65 |
| LFFLGTISLSLCQDDQERC | NSY-4 | SEQ ID NO: 66 |
| FFLGTISLSLCQDDQERC | NSY-5 | SEQ ID NO: 67 |
| FLGTISLSLCQDDQERC | NSY-6 | SEQ ID NO: 68 |
| LGTISLSLCQDDQERC | NSY-7 | SEQ ID NO: 69 |
| GTISLSLCQDDQERC | NSY-8 | SEQ ID NO: 70 |
| TISLSLCQDDQERC | NSY-9 | SEQ ID NO: 71 |
| ISLSLCQDDQERC | NSY-10 | SEQ ID NO: 72 |
| LSLCQDDQERC | NSY-11 | SEQ ID NO: 73 |
| SLCQDDQERC | NSY-12 | SEQ ID NO: 74 |
| LCQDDQERC | NSY-13 | SEQ ID NO: 75 |
| CQDDQERC | NSY-14 | SEQ ID NO: 76 |
| QDDQERC | NSY-15 | SEQ ID NO: 77 |

Unless defined otherwise, all technical and scientific terms used herein have the same meanings as commonly understood by one of skill in the art to which the disclosed disclosure belongs. Publications cited herein and the materials for which they are cited are specifically incorporated by reference.

Those skilled in the art will recognize, or be able to ascertain using no more than routine experimentation, many equivalents to the specific embodiments of the disclosure described herein. Such equivalents are intended to be encompassed by the following claims.

The invention claimed is:

1. An isolated polypeptide consisting of the amino acid sequence

SMLLLFFLGTISLSLCQDDQERC, (SEQ ID NO: 1)

SMLLLFFLGTISLSLCQ, (SEQ ID NO: 56)

PMLLLFFLGTISLSLCQ, (SEQ ID NO: 57)
or

LLFFLGTISLSLCQDDQERC, (SEQ ID NO: 65)

wherein the polypeptide is acetylated or amidated.

2. A composition comprising an effective amount of the polypeptide of claim 1, and pharmaceutically acceptable carrier.

3. The composition of claim 2, further comprising another antiviral compound.

4. The composition of claim 2, wherein the composition is in the form of a capsule, tablet, pill, powder, granule, or gel.

5. The composition of claim 2, wherein the composition is in the form of a sterilized pH buffered aqueous salt solution.

* * * * *

SEQUENCE LISTING

<160> NUMBER OF SEQ ID NOS: 82

<210> SEQ ID NO 1
<211> LENGTH: 23
<212> TYPE: PRT
<213> ORGANISM: Artificial
<220> FEATURE:
<223> OTHER INFORMATION: Synthetic

<400> SEQUENCE: 1

Ser Met Leu Leu Leu Phe Phe Leu Gly Thr Ile Ser Leu Ser Leu Cys
1               5                   10                  15

Gln Asp Asp Gln Glu Arg Cys
            20

<210> SEQ ID NO 2
<211> LENGTH: 23
<212> TYPE: PRT
<213> ORGANISM: Artificial
<220> FEATURE:
<223> OTHER INFORMATION: Synthetic

<400> SEQUENCE: 2

Ala Met Leu Leu Leu Phe Phe Leu Gly Thr Ile Ser Leu Ser Leu Cys
1               5                   10                  15

Gln Asp Asp Gln Glu Arg Cys
            20

<210> SEQ ID NO 3
<211> LENGTH: 23
<212> TYPE: PRT
<213> ORGANISM: Artificial
<220> FEATURE:
<223> OTHER INFORMATION: Synthetic

<400> SEQUENCE: 3

Ser Ala Leu Leu Leu Phe Phe Leu Gly Thr Ile Ser Leu Ser Leu Cys
1               5                   10                  15

Gln Asp Asp Gln Glu Arg Cys
            20

<210> SEQ ID NO 4
<211> LENGTH: 23
<212> TYPE: PRT
<213> ORGANISM: Artificial
<220> FEATURE:
<223> OTHER INFORMATION: Synthetic

<400> SEQUENCE: 4

Ser Met Ala Leu Leu Phe Phe Leu Gly Thr Ile Ser Leu Ser Leu Cys
1               5                   10                  15

Gln Asp Asp Gln Glu Arg Cys
            20

<210> SEQ ID NO 5
<211> LENGTH: 23
<212> TYPE: PRT
<213> ORGANISM: Artificial
<220> FEATURE:
<223> OTHER INFORMATION: Synthetic

<400> SEQUENCE: 5

Ser Met Leu Ala Leu Phe Phe Leu Gly Thr Ile Ser Leu Ser Leu Cys
1               5                   10                  15

Gln Asp Asp Gln Glu Arg Cys
            20

<210> SEQ ID NO 6
<211> LENGTH: 23
<212> TYPE: PRT
<213> ORGANISM: Artificial
<220> FEATURE:
<223> OTHER INFORMATION: Synthetic

<400> SEQUENCE: 6

Ser Met Leu Leu Ala Phe Phe Leu Gly Thr Ile Ser Leu Ser Leu Cys
1               5                   10                  15

Gln Asp Asp Gln Glu Arg Cys
            20

<210> SEQ ID NO 7
<211> LENGTH: 23
<212> TYPE: PRT
<213> ORGANISM: Artificial
<220> FEATURE:
<223> OTHER INFORMATION: Synthetic

<400> SEQUENCE: 7

Ser Met Leu Leu Leu Ala Phe Leu Gly Thr Ile Ser Leu Ser Leu Cys
1               5                   10                  15

Gln Asp Asp Gln Glu Arg Cys
            20

<210> SEQ ID NO 8
<211> LENGTH: 23
<212> TYPE: PRT
<213> ORGANISM: Artificial
<220> FEATURE:
<223> OTHER INFORMATION: Synthetic

<400> SEQUENCE: 8

Ser Met Leu Leu Leu Phe Ala Leu Gly Thr Ile Ser Leu Ser Leu Cys
1               5                   10                  15

Gln Asp Asp Gln Glu Arg Cys
            20

<210> SEQ ID NO 9
<211> LENGTH: 23
<212> TYPE: PRT
<213> ORGANISM: Artificial
<220> FEATURE:
<223> OTHER INFORMATION: Synthetic

<400> SEQUENCE: 9

Ser Met Leu Leu Leu Phe Phe Ala Gly Thr Ile Ser Leu Ser Leu Cys
1               5                   10                  15

Gln Asp Asp Gln Glu Arg Cys
            20

<210> SEQ ID NO 10
<211> LENGTH: 23
<212> TYPE: PRT
<213> ORGANISM: Artificial
<220> FEATURE:
<223> OTHER INFORMATION: Synthetic

<400> SEQUENCE: 10

Ser Met Leu Leu Leu Phe Phe Leu Ala Thr Ile Ser Leu Ser Leu Cys
1               5                   10                  15

Gln Asp Asp Gln Glu Arg Cys
            20

<210> SEQ ID NO 11
<211> LENGTH: 23
<212> TYPE: PRT
<213> ORGANISM: Artificial
<220> FEATURE:
<223> OTHER INFORMATION: Synthetic

<400> SEQUENCE: 11

Ser Met Leu Leu Leu Phe Phe Leu Gly Ala Ile Ser Leu Ser Leu Cys
1               5                   10                  15

Gln Asp Asp Gln Glu Arg Cys
            20

<210> SEQ ID NO 12
<211> LENGTH: 23
<212> TYPE: PRT
<213> ORGANISM: Artificial
<220> FEATURE:
<223> OTHER INFORMATION: Synthetic

<400> SEQUENCE: 12

Ser Met Leu Leu Leu Phe Phe Leu Gly Thr Ala Ser Leu Ser Leu Cys
1               5                   10                  15

Gln Asp Asp Gln Glu Arg Cys
            20

<210> SEQ ID NO 13
<211> LENGTH: 23
<212> TYPE: PRT
<213> ORGANISM: Artificial
<220> FEATURE:
<223> OTHER INFORMATION: Synthetic

<400> SEQUENCE: 13

Ser Met Leu Leu Leu Phe Phe Leu Gly Thr Ile Ala Leu Ser Leu Cys
1               5                   10                  15

Gln Asp Asp Gln Glu Arg Cys
            20

<210> SEQ ID NO 14
<211> LENGTH: 23
<212> TYPE: PRT
<213> ORGANISM: Artificial
<220> FEATURE:
<223> OTHER INFORMATION: Synthetic

<400> SEQUENCE: 14

Ser Met Leu Leu Leu Phe Phe Leu Gly Thr Ile Ser Ala Ser Leu Cys
1               5                   10                  15

Gln Asp Asp Gln Glu Arg Cys
            20

<210> SEQ ID NO 15
<211> LENGTH: 23
<212> TYPE: PRT
<213> ORGANISM: Artificial
<220> FEATURE:
<223> OTHER INFORMATION: Synthetic

<400> SEQUENCE: 15

Ser Met Leu Leu Leu Phe Phe Leu Gly Thr Ile Ser Leu Ala Leu Cys

```
<210> SEQ ID NO 16
<211> LENGTH: 23
<212> TYPE: PRT
<213> ORGANISM: Artificial
<220> FEATURE:
<223> OTHER INFORMATION: Synthetic

<400> SEQUENCE: 16

Ser Met Leu Leu Leu Phe Phe Leu Gly Thr Ile Ser Leu Ser Ala Cys
1               5                   10                  15

Gln Asp Asp Gln Glu Arg Cys
            20

<210> SEQ ID NO 17
<211> LENGTH: 23
<212> TYPE: PRT
<213> ORGANISM: Artificial
<220> FEATURE:
<223> OTHER INFORMATION: Synthetic

<400> SEQUENCE: 17

Ser Met Leu Leu Leu Phe Phe Leu Gly Thr Ile Ser Leu Ser Leu Ala
1               5                   10                  15

Gln Asp Asp Gln Glu Arg Cys
            20

<210> SEQ ID NO 18
<211> LENGTH: 23
<212> TYPE: PRT
<213> ORGANISM: Artificial
<220> FEATURE:
<223> OTHER INFORMATION: Synthetic

<400> SEQUENCE: 18

Ser Met Leu Leu Leu Phe Phe Leu Gly Thr Ile Ser Leu Ser Leu Cys
1               5                   10                  15

Ala Asp Asp Gln Glu Arg Cys
            20

<210> SEQ ID NO 19
<211> LENGTH: 23
<212> TYPE: PRT
<213> ORGANISM: Artificial
<220> FEATURE:
<223> OTHER INFORMATION: Synthetic

<400> SEQUENCE: 19

Ser Met Leu Leu Leu Phe Phe Leu Gly Thr Ile Ser Leu Ser Leu Cys
1               5                   10                  15

Gln Ala Asp Gln Glu Arg Cys
            20

<210> SEQ ID NO 20
<211> LENGTH: 23
<212> TYPE: PRT
<213> ORGANISM: Artificial
<220> FEATURE:
<223> OTHER INFORMATION: Synthetic

<400> SEQUENCE: 20
```

Ser Met Leu Leu Leu Phe Phe Leu Gly Thr Ile Ser Leu Ser Leu Cys
1               5                   10                  15

Gln Asp Ala Gln Glu Arg Cys
            20

<210> SEQ ID NO 21
<211> LENGTH: 23
<212> TYPE: PRT
<213> ORGANISM: Artificial
<220> FEATURE:
<223> OTHER INFORMATION: Synthetic

<400> SEQUENCE: 21

Ser Met Leu Leu Leu Phe Phe Leu Gly Thr Ile Ser Leu Ser Leu Cys
1               5                   10                  15

Gln Asp Asp Ala Glu Arg Cys
            20

<210> SEQ ID NO 22
<211> LENGTH: 23
<212> TYPE: PRT
<213> ORGANISM: Artificial
<220> FEATURE:
<223> OTHER INFORMATION: Synthetic

<400> SEQUENCE: 22

Ser Met Leu Leu Leu Phe Phe Leu Gly Thr Ile Ser Leu Ser Leu Cys
1               5                   10                  15

Gln Asp Asp Gln Ala Arg Cys
            20

<210> SEQ ID NO 23
<211> LENGTH: 23
<212> TYPE: PRT
<213> ORGANISM: Artificial
<220> FEATURE:
<223> OTHER INFORMATION: Synthetic

<400> SEQUENCE: 23

Ser Met Leu Leu Leu Phe Phe Leu Gly Thr Ile Ser Leu Ser Leu Cys
1               5                   10                  15

Gln Asp Asp Gln Glu Ala Cys
            20

<210> SEQ ID NO 24
<211> LENGTH: 23
<212> TYPE: PRT
<213> ORGANISM: Artificial
<220> FEATURE:
<223> OTHER INFORMATION: Synthetic

<400> SEQUENCE: 24

Ser Met Leu Leu Leu Phe Phe Leu Gly Thr Ile Ser Leu Ser Leu Cys
1               5                   10                  15

Gln Asp Asp Gln Glu Arg Ala
            20

<210> SEQ ID NO 25
<211> LENGTH: 22
<212> TYPE: PRT
<213> ORGANISM: Artificial
<220> FEATURE:
<223> OTHER INFORMATION: Synthetic

<400> SEQUENCE: 25

```
Ser Met Leu Leu Leu Phe Phe Leu Gly Thr Ile Ser Leu Ser Leu Cys
1               5                   10                  15

Gln Asp Glu Arg Gly Ala
            20

<210> SEQ ID NO 26
<211> LENGTH: 21
<212> TYPE: PRT
<213> ORGANISM: Artificial
<220> FEATURE:
<223> OTHER INFORMATION: Synthetic

<400> SEQUENCE: 26

Ser Met Leu Leu Leu Phe Phe Leu Gly Thr Ile Ser Leu Ser Leu Cys
1               5                   10                  15

Gln Asp Glu Gly Ala
            20

<210> SEQ ID NO 27
<211> LENGTH: 23
<212> TYPE: PRT
<213> ORGANISM: Artificial
<220> FEATURE:
<223> OTHER INFORMATION: Synthetic

<400> SEQUENCE: 27

Ser Met Leu Leu Leu Phe Phe Leu Gly Thr Ile Ser Leu Ser Leu Cys
1               5                   10                  15

Gln Glu Glu Glu Arg Gly Ala
            20

<210> SEQ ID NO 28
<211> LENGTH: 22
<212> TYPE: PRT
<213> ORGANISM: Artificial
<220> FEATURE:
<223> OTHER INFORMATION: Synthetic

<400> SEQUENCE: 28

Ser Met Leu Leu Leu Phe Phe Leu Gly Thr Ile Ser Leu Ser Leu Cys
1               5                   10                  15

Glu Gln Glu Arg Asn Ala
            20

<210> SEQ ID NO 29
<211> LENGTH: 23
<212> TYPE: PRT
<213> ORGANISM: Artificial
<220> FEATURE:
<223> OTHER INFORMATION: Synthetic

<400> SEQUENCE: 29

Ser Met Leu Leu Leu Phe Phe Leu Gly Thr Ile Ser Leu Ser Leu Cys
1               5                   10                  15

Glu Gln Glu Arg Asp Ser Asp
            20

<210> SEQ ID NO 30
<211> LENGTH: 23
<212> TYPE: PRT
<213> ORGANISM: Artificial
<220> FEATURE:
<223> OTHER INFORMATION: Synthetic
```

```
<400> SEQUENCE: 30

Ser Met Leu Leu Leu Phe Phe Leu Gly Thr Ile Ser Leu Ser Leu Cys
1               5                   10                  15

Glu Gln Glu Arg Asp Ala Asp
            20

<210> SEQ ID NO 31
<211> LENGTH: 22
<212> TYPE: PRT
<213> ORGANISM: Artificial
<220> FEATURE:
<223> OTHER INFORMATION: Synthetic

<400> SEQUENCE: 31

Ser Met Leu Leu Leu Phe Phe Leu Gly Thr Ile Ser Leu Ser Leu Cys
1               5                   10                  15

Gln Glu Glu Arg Gly Ala
            20

<210> SEQ ID NO 32
<211> LENGTH: 22
<212> TYPE: PRT
<213> ORGANISM: Artificial
<220> FEATURE:
<223> OTHER INFORMATION: Synthetic

<400> SEQUENCE: 32

Ser Met Leu Leu Leu Phe Phe Leu Gly Thr Ile Ser Leu Ser Leu Cys
1               5                   10                  15

Glu Glu Glu Arg Asn Ala
            20

<210> SEQ ID NO 33
<211> LENGTH: 22
<212> TYPE: PRT
<213> ORGANISM: Artificial
<220> FEATURE:
<223> OTHER INFORMATION: Synthetic

<400> SEQUENCE: 33

Ser Met Leu Leu Leu Phe Phe Leu Gly Thr Ile Ser Leu Ser Leu Cys
1               5                   10                  15

Gln Glu Glu Arg Asp Ala
            20

<210> SEQ ID NO 34
<211> LENGTH: 22
<212> TYPE: PRT
<213> ORGANISM: Artificial
<220> FEATURE:
<223> OTHER INFORMATION: Synthetic

<400> SEQUENCE: 34

Ser Leu Leu Leu Leu Phe Phe Leu Gly Thr Ile Ser Leu Ser Leu Cys
1               5                   10                  15

Gln Asp Glu Thr Asn Ala
            20

<210> SEQ ID NO 35
<211> LENGTH: 23
<212> TYPE: PRT
<213> ORGANISM: Artificial
<220> FEATURE:
<223> OTHER INFORMATION: Synthetic
```

<400> SEQUENCE: 35

Ser Leu Leu Leu Leu Phe Phe Leu Gly Thr Ile Asn Leu Ser Leu Cys
1               5                   10                  15

Gln Asp Asp Glu Met Pro Lys
            20

<210> SEQ ID NO 36
<211> LENGTH: 23
<212> TYPE: PRT
<213> ORGANISM: Artificial
<220> FEATURE:
<223> OTHER INFORMATION: Synthetic

<400> SEQUENCE: 36

Pro Met Leu Leu Leu Phe Phe Leu Gly Thr Ile Ser Leu Ser Leu Cys
1               5                   10                  15

Gln Glu Glu Glu Arg Gly Ala
            20

<210> SEQ ID NO 37
<211> LENGTH: 22
<212> TYPE: PRT
<213> ORGANISM: Artificial
<220> FEATURE:
<223> OTHER INFORMATION: Synthetic

<400> SEQUENCE: 37

Ser Met Leu Leu Leu Phe Phe Leu Gly Thr Ile Asn Leu Ser Leu Cys
1               5                   10                  15

Gln Glu Glu Arg Asp Ala
            20

<210> SEQ ID NO 38
<211> LENGTH: 23
<212> TYPE: PRT
<213> ORGANISM: Artificial
<220> FEATURE:
<223> OTHER INFORMATION: Synthetic

<400> SEQUENCE: 38

Ser Leu Leu Leu Leu Phe Phe Leu Gly Thr Ile Ser Leu Ser Leu Cys
1               5                   10                  15

Gln Glu Glu Glu Arg Asn Ala
            20

<210> SEQ ID NO 39
<211> LENGTH: 22
<212> TYPE: PRT
<213> ORGANISM: Artificial
<220> FEATURE:
<223> OTHER INFORMATION: Synthetic

<400> SEQUENCE: 39

Ser Met Leu Leu Leu Phe Phe Leu Gly Met Ile Ser Leu Ser Leu Cys
1               5                   10                  15

Gln Asp Glu Arg Gly Ala
            20

<210> SEQ ID NO 40
<211> LENGTH: 21
<212> TYPE: PRT
<213> ORGANISM: Artificial
<220> FEATURE:

<223> OTHER INFORMATION: Synthetic

<400> SEQUENCE: 40

Met Leu Leu Leu Phe Phe Leu Gly Thr Ile Ser Leu Ser Leu Cys Glu
1               5                   10                  15

Gln Glu Arg Asn Ala
            20

<210> SEQ ID NO 41
<211> LENGTH: 22
<212> TYPE: PRT
<213> ORGANISM: Artificial
<220> FEATURE:
<223> OTHER INFORMATION: Synthetic

<400> SEQUENCE: 41

Ser Met Leu Leu Leu Phe Phe Leu Gly Thr Ile Asn Leu Ser Leu Cys
1               5                   10                  15

Glu Gln Glu Arg Asp Ala
            20

<210> SEQ ID NO 42
<211> LENGTH: 22
<212> TYPE: PRT
<213> ORGANISM: Artificial
<220> FEATURE:
<223> OTHER INFORMATION: Synthetic

<400> SEQUENCE: 42

Pro Met Leu Leu Leu Phe Phe Leu Gly Thr Ile Ser Leu Ser Leu Cys
1               5                   10                  15

Glu Gln Glu Arg Asn Ala
            20

<210> SEQ ID NO 43
<211> LENGTH: 22
<212> TYPE: PRT
<213> ORGANISM: Artificial
<220> FEATURE:
<223> OTHER INFORMATION: Synthetic

<400> SEQUENCE: 43

Ser Met Leu Leu Leu Phe Phe Leu Gly Thr Ile Asn Leu Ser Leu Cys
1               5                   10                  15

Glu Gln Glu Arg Asn Ala
            20

<210> SEQ ID NO 44
<211> LENGTH: 21
<212> TYPE: PRT
<213> ORGANISM: Artificial
<220> FEATURE:
<223> OTHER INFORMATION: Synthetic

<400> SEQUENCE: 44

Ser Leu Leu Leu Leu Phe Phe Leu Gly Thr Ile Ser Leu Ser Leu Cys
1               5                   10                  15

Gln Arg Glu Ala Asp
            20

<210> SEQ ID NO 45
<211> LENGTH: 22
<212> TYPE: PRT
<213> ORGANISM: Artificial

```
<220> FEATURE:
<223> OTHER INFORMATION: Synthetic

<400> SEQUENCE: 45

Pro Met Leu Leu Leu Phe Phe Leu Gly Thr Ile Ser Leu Ser Leu Cys
1               5                   10                  15
Gln Glu Glu Arg Gly Ala
            20

<210> SEQ ID NO 46
<211> LENGTH: 22
<212> TYPE: PRT
<213> ORGANISM: Artificial
<220> FEATURE:
<223> OTHER INFORMATION: Synthetic

<400> SEQUENCE: 46

Ser Leu Leu Leu Leu Phe Phe Leu Gly Thr Ile Asn Leu Ser Leu Cys
1               5                   10                  15
Gln Asp Glu Thr Asn Ala
            20

<210> SEQ ID NO 47
<211> LENGTH: 22
<212> TYPE: PRT
<213> ORGANISM: Artificial
<220> FEATURE:
<223> OTHER INFORMATION: Synthetic

<400> SEQUENCE: 47

Ser Met Leu Leu Leu Phe Phe Leu Gly Thr Ile Asn Leu Ser Leu Cys
1               5                   10                  15
Glu Glu Glu Arg Asp Ala
            20

<210> SEQ ID NO 48
<211> LENGTH: 20
<212> TYPE: PRT
<213> ORGANISM: Artificial
<220> FEATURE:
<223> OTHER INFORMATION: Synthetic

<400> SEQUENCE: 48

Ser Met Leu Leu Leu Phe Phe Leu Gly Thr Ile Ser Leu Ser Leu Cys
1               5                   10                  15
Glu Glu Glu Arg
            20

<210> SEQ ID NO 49
<211> LENGTH: 22
<212> TYPE: PRT
<213> ORGANISM: Artificial
<220> FEATURE:
<223> OTHER INFORMATION: Synthetic

<400> SEQUENCE: 49

Ser Met Leu Leu Leu Phe Phe Leu Gly Thr Ile Ser Leu Ser Leu Cys
1               5                   10                  15
Glu Glu Glu Arg Asp Ala
            20

<210> SEQ ID NO 50
<211> LENGTH: 22
<212> TYPE: PRT
```

```
<213> ORGANISM: Artificial
<220> FEATURE:
<223> OTHER INFORMATION: Synthetic

<400> SEQUENCE: 50

Ser Met Leu Leu Leu Phe Phe Leu Gly Thr Ile Ser Leu Ser Leu Cys
1               5                   10                  15

Glu Glu Glu Arg Ser Ala
            20

<210> SEQ ID NO 51
<211> LENGTH: 22
<212> TYPE: PRT
<213> ORGANISM: Artificial
<220> FEATURE:
<223> OTHER INFORMATION: Synthetic

<400> SEQUENCE: 51

Ser Met Leu Leu Leu Phe Phe Leu Gly Thr Ile Ser Leu Ser Leu Cys
1               5                   10                  15

Glu Glu Glu Arg Asn Ala
            20

<210> SEQ ID NO 52
<211> LENGTH: 22
<212> TYPE: PRT
<213> ORGANISM: Artificial
<220> FEATURE:
<223> OTHER INFORMATION: Synthetic

<400> SEQUENCE: 52

Ser Met Leu Leu Leu Phe Phe Leu Gly Thr Ile Ser Leu Ser Leu Cys
1               5                   10                  15

Glu Glu Glu Arg Gly Ala
            20

<210> SEQ ID NO 53
<211> LENGTH: 23
<212> TYPE: PRT
<213> ORGANISM: Artificial
<220> FEATURE:
<223> OTHER INFORMATION: Synthetic

<400> SEQUENCE: 53

Ser Met Leu Leu Phe Phe Phe Leu Gly Thr Ile Ser Leu Ser Leu Cys
1               5                   10                  15

Gln Glu Glu Glu Arg Gly Ala
            20

<210> SEQ ID NO 54
<211> LENGTH: 22
<212> TYPE: PRT
<213> ORGANISM: Artificial
<220> FEATURE:
<223> OTHER INFORMATION: Synthetic

<400> SEQUENCE: 54

Ser Leu Leu Leu Leu Phe Phe Leu Gly Thr Ile Ser Leu Ser Leu Cys
1               5                   10                  15

Glu Glu Glu Arg Asn Ala
            20

<210> SEQ ID NO 55
<211> LENGTH: 22
```

```
<212> TYPE: PRT
<213> ORGANISM: Artificial
<220> FEATURE:
<223> OTHER INFORMATION: Synthetic

<400> SEQUENCE: 55

Ser Met Leu Leu Ile Phe Phe Leu Gly Thr Ile Ser Leu Ser Leu Cys
1               5                   10                  15
Glu Gln Glu Arg Asp Ala
            20

<210> SEQ ID NO 56
<211> LENGTH: 17
<212> TYPE: PRT
<213> ORGANISM: Artificial
<220> FEATURE:
<223> OTHER INFORMATION: Synthetic

<400> SEQUENCE: 56

Ser Met Leu Leu Leu Phe Phe Leu Gly Thr Ile Ser Leu Ser Leu Cys
1               5                   10                  15
Gln

<210> SEQ ID NO 57
<211> LENGTH: 17
<212> TYPE: PRT
<213> ORGANISM: Artificial
<220> FEATURE:
<223> OTHER INFORMATION: Synthetic

<400> SEQUENCE: 57

Pro Met Leu Leu Leu Phe Phe Leu Gly Thr Ile Ser Leu Ser Leu Cys
1               5                   10                  15
Gln

<210> SEQ ID NO 58
<211> LENGTH: 23
<212> TYPE: PRT
<213> ORGANISM: Artificial
<220> FEATURE:
<223> OTHER INFORMATION: Synthetic

<400> SEQUENCE: 58

Pro Met Leu Leu Leu Phe Phe Leu Gly Thr Ile Ser Leu Ser Leu Cys
1               5                   10                  15
Gln Asp Asp Gln Glu Arg Cys
            20

<210> SEQ ID NO 59
<211> LENGTH: 22
<212> TYPE: PRT
<213> ORGANISM: Artificial
<220> FEATURE:
<223> OTHER INFORMATION: Synthetic

<400> SEQUENCE: 59

Ser Met Leu Leu Leu Phe Phe Leu Gly Thr Ile Ser Leu Ser Leu Cys
1               5                   10                  15
Gln Asp Asp Gln Glu Arg
            20

<210> SEQ ID NO 60
<211> LENGTH: 21
<212> TYPE: PRT
```

```
<213> ORGANISM: Artificial
<220> FEATURE:
<223> OTHER INFORMATION: Synthetic

<400> SEQUENCE: 60

Ser Met Leu Leu Leu Phe Phe Leu Gly Thr Ile Ser Leu Ser Leu Cys
1               5                   10                  15

Gln Asp Asp Gln Glu
            20

<210> SEQ ID NO 61
<211> LENGTH: 20
<212> TYPE: PRT
<213> ORGANISM: Artificial
<220> FEATURE:
<223> OTHER INFORMATION: Synthetic

<400> SEQUENCE: 61

Ser Met Leu Leu Leu Phe Phe Leu Gly Thr Ile Ser Leu Ser Leu Cys
1               5                   10                  15

Gln Asp Asp Gln
            20

<210> SEQ ID NO 62
<211> LENGTH: 19
<212> TYPE: PRT
<213> ORGANISM: Artificial
<220> FEATURE:
<223> OTHER INFORMATION: Synthetic

<400> SEQUENCE: 62

Ser Met Leu Leu Leu Phe Phe Leu Gly Thr Ile Ser Leu Ser Leu Cys
1               5                   10                  15

Gln Asp Asp

<210> SEQ ID NO 63
<211> LENGTH: 22
<212> TYPE: PRT
<213> ORGANISM: Artificial
<220> FEATURE:
<223> OTHER INFORMATION: Synthetic

<400> SEQUENCE: 63

Met Leu Leu Leu Phe Phe Leu Gly Thr Ile Ser Leu Ser Leu Cys Gln
1               5                   10                  15

Asp Asp Gln Glu Arg Cys
            20

<210> SEQ ID NO 64
<211> LENGTH: 21
<212> TYPE: PRT
<213> ORGANISM: Artificial
<220> FEATURE:
<223> OTHER INFORMATION: Synthetic

<400> SEQUENCE: 64

Leu Leu Leu Phe Phe Leu Gly Thr Ile Ser Leu Ser Leu Cys Gln Asp
1               5                   10                  15

Asp Gln Glu Arg Cys
            20

<210> SEQ ID NO 65
<211> LENGTH: 20
<212> TYPE: PRT
```

<213> ORGANISM: Artificial
<220> FEATURE:
<223> OTHER INFORMATION: Synthetic

<400> SEQUENCE: 65

Leu Leu Phe Phe Leu Gly Thr Ile Ser Leu Ser Leu Cys Gln Asp Asp
1               5                   10                  15

Gln Glu Arg Cys
            20

<210> SEQ ID NO 66
<211> LENGTH: 19
<212> TYPE: PRT
<213> ORGANISM: Artificial
<220> FEATURE:
<223> OTHER INFORMATION: Synthetic

<400> SEQUENCE: 66

Leu Phe Phe Leu Gly Thr Ile Ser Leu Ser Leu Cys Gln Asp Asp Gln
1               5                   10                  15

Glu Arg Cys

<210> SEQ ID NO 67
<211> LENGTH: 18
<212> TYPE: PRT
<213> ORGANISM: Artificial
<220> FEATURE:
<223> OTHER INFORMATION: Synthetic

<400> SEQUENCE: 67

Phe Phe Leu Gly Thr Ile Ser Leu Ser Leu Cys Gln Asp Asp Gln Glu
1               5                   10                  15

Arg Cys

<210> SEQ ID NO 68
<211> LENGTH: 17
<212> TYPE: PRT
<213> ORGANISM: Artificial
<220> FEATURE:
<223> OTHER INFORMATION: Synthetic

<400> SEQUENCE: 68

Phe Leu Gly Thr Ile Ser Leu Ser Leu Cys Gln Asp Asp Gln Glu Arg
1               5                   10                  15

Cys

<210> SEQ ID NO 69
<211> LENGTH: 16
<212> TYPE: PRT
<213> ORGANISM: Artificial
<220> FEATURE:
<223> OTHER INFORMATION: Synthetic

<400> SEQUENCE: 69

Leu Gly Thr Ile Ser Leu Ser Leu Cys Gln Asp Asp Gln Glu Arg Cys
1               5                   10                  15

<210> SEQ ID NO 70
<211> LENGTH: 15
<212> TYPE: PRT
<213> ORGANISM: Artificial
<220> FEATURE:
<223> OTHER INFORMATION: Synthetic

<400> SEQUENCE: 70

Gly Thr Ile Ser Leu Ser Leu Cys Gln Asp Asp Gln Glu Arg Cys
1               5                   10                  15

<210> SEQ ID NO 71
<211> LENGTH: 14
<212> TYPE: PRT
<213> ORGANISM: Artificial
<220> FEATURE:
<223> OTHER INFORMATION: Synthetic

<400> SEQUENCE: 71

Thr Ile Ser Leu Ser Leu Cys Gln Asp Asp Gln Glu Arg Cys
1               5                   10

<210> SEQ ID NO 72
<211> LENGTH: 13
<212> TYPE: PRT
<213> ORGANISM: Artificial
<220> FEATURE:
<223> OTHER INFORMATION: Synthetic

<400> SEQUENCE: 72

Ile Ser Leu Ser Leu Cys Gln Asp Asp Gln Glu Arg Cys
1               5                   10

<210> SEQ ID NO 73
<211> LENGTH: 11
<212> TYPE: PRT
<213> ORGANISM: Artificial
<220> FEATURE:
<223> OTHER INFORMATION: Synthetic

<400> SEQUENCE: 73

Leu Ser Leu Cys Gln Asp Asp Gln Glu Arg Cys
1               5                   10

<210> SEQ ID NO 74
<211> LENGTH: 10
<212> TYPE: PRT
<213> ORGANISM: Artificial
<220> FEATURE:
<223> OTHER INFORMATION: Synthetic

<400> SEQUENCE: 74

Ser Leu Cys Gln Asp Asp Gln Glu Arg Cys
1               5                   10

<210> SEQ ID NO 75
<211> LENGTH: 9
<212> TYPE: PRT
<213> ORGANISM: Artificial
<220> FEATURE:
<223> OTHER INFORMATION: Synthetic

<400> SEQUENCE: 75

Leu Cys Gln Asp Asp Gln Glu Arg Cys
1               5

<210> SEQ ID NO 76
<211> LENGTH: 8
<212> TYPE: PRT
<213> ORGANISM: Artificial
<220> FEATURE:
<223> OTHER INFORMATION: Synthetic

<400> SEQUENCE: 76

Cys Gln Asp Asp Gln Glu Arg Cys
1               5

<210> SEQ ID NO 77
<211> LENGTH: 7
<212> TYPE: PRT
<213> ORGANISM: Artificial
<220> FEATURE:
<223> OTHER INFORMATION: Synthetic

<400> SEQUENCE: 77

Gln Asp Asp Gln Glu Arg Cys
1               5

<210> SEQ ID NO 78
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (1)..(12)
<223> OTHER INFORMATION: X is any amino acid

<400> SEQUENCE: 78

Leu Phe Phe Xaa Gly Thr Ile Xaa Leu Xaa Leu Cys
1               5                   10

<210> SEQ ID NO 79
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (1)..(15)
<223> OTHER INFORMATION: X is any amino acid

<400> SEQUENCE: 79

Leu Phe Phe Xaa Gly Thr Ile Xaa Leu Xaa Leu Cys Xaa Asp Asp
1               5                   10                  15

<210> SEQ ID NO 80
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (1)..(19)
<223> OTHER INFORMATION: X is any amino acid

<400> SEQUENCE: 80

Leu Phe Phe Xaa Gly Thr Ile Xaa Leu Xaa Leu Cys Xaa Asp Asp Gln
1               5                   10                  15

Glu Arg Cys

<210> SEQ ID NO 81
<211> LENGTH: 6
<212> TYPE: PRT
<213> ORGANISM: Artificial
<220> FEATURE:
<223> OTHER INFORMATION: Synthetic

<400> SEQUENCE: 81

```
Asp Asp Gln Glu Arg Cys
1               5

<210> SEQ ID NO 82
<211> LENGTH: 6
<212> TYPE: PRT
<213> ORGANISM: Artificial
<220> FEATURE:
<223> OTHER INFORMATION: Synthetic

<400> SEQUENCE: 82

Glu Glu Glu Arg Gly Ala
1               5
```